US008382738B2

(12) United States Patent
Simpson et al.

(10) Patent No.: US 8,382,738 B2
(45) Date of Patent: Feb. 26, 2013

(54) BALLOON CATHETER TAPERED SHAFT HAVING HIGH STRENGTH AND FLEXIBILITY AND METHOD OF MAKING SAME

(75) Inventors: John A. Simpson, Carlsbad, CA (US); Jonathan P. Durcan, Temecula, CA (US); Bruce M. Wilson, Temecula, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 11/763,623

(22) Filed: Jun. 15, 2007

(65) Prior Publication Data

US 2008/0045928 A1     Feb. 21, 2008

Related U.S. Application Data

(63) Continuation-in-part of application No. 11/480,143, filed on Jun. 30, 2006, now Pat. No. 7,906,066.

(51) Int. Cl.
*A61M 29/00* (2006.01)
*A61M 31/00* (2006.01)
*A61M 37/00* (2006.01)
*A61M 25/00* (2006.01)

(52) U.S. Cl. .............. 604/523; 604/96.01; 604/103.04

(58) Field of Classification Search ........... 604/523–527, 604/264, 96.01
See application file for complete search history.

(56) References Cited

U.S. PATENT DOCUMENTS

| | | | |
|---|---|---|---|
| 4,425,919 A | 1/1984 | Alston et al. | |
| 4,563,181 A | 1/1986 | Wijayarathna et al. | |
| 4,596,563 A | 6/1986 | Pande | |
| 4,775,371 A | 10/1988 | Mueller, Jr. | |
| 4,820,349 A | 4/1989 | Saab et al. | |
| 4,877,031 A | 10/1989 | Conway et al. | |
| 4,886,506 A | 12/1989 | Lovgren et al. | |
| 4,892,519 A | 1/1990 | Songer et al. | |
| 4,952,357 A | 8/1990 | Euteneuer | |
| 4,960,410 A * | 10/1990 | Pinchuk .................. 604/96.01 |
| 4,976,720 A | 12/1990 | Machold et al. | |
| 5,047,045 A | 9/1991 | Arney et al. | |
| 5,061,273 A | 10/1991 | Yock | |
| 5,078,702 A | 1/1992 | Pomeranz | |
| 5,085,649 A | 2/1992 | Flynn | |

(Continued)

FOREIGN PATENT DOCUMENTS

EP    0 277 368 A    8/1988
EP      0414350 A    2/1991

(Continued)

OTHER PUBLICATIONS

U.S. Appl. No. 11/480,143, filed Jun. 30, 2008—Requirement for Restriction/Election.

(Continued)

*Primary Examiner* — Kevin C Sirmons
*Assistant Examiner* — Andrew Gilbert
(74) *Attorney, Agent, or Firm* — Baker Botts L.L.P.

(57) ABSTRACT

A catheter having an elongated shaft with a tubular member which forms at least a portion of the shaft and which is formed of a biaxially oriented thermoplastic polymeric material, and a method of forming the catheter shaft by radially and longitudinally expanding the tubular member to biaxially orient the polymeric material, and, in one embodiment, tapering the tubular member to form a bending stiffness transition. A catheter of the invention has an improved combination of low bending stiffness, high rupture pressure, and high tensile strength, for improved catheter performance.

19 Claims, 6 Drawing Sheets

U.S. PATENT DOCUMENTS

| | | |
|---|---|---|
| 5,112,304 A | 5/1992 | Barlow et al. |
| 5,156,594 A | 10/1992 | Keith |
| 5,176,661 A | 1/1993 | Evard et al. |
| 5,195,969 A | 3/1993 | Wang et al. |
| 5,205,822 A | 4/1993 | Johnson et al. |
| 5,207,700 A | 5/1993 | Euteneuer |
| 5,209,232 A | 5/1993 | Levene |
| 5,217,434 A | 6/1993 | Arney |
| 5,217,482 A | 6/1993 | Keith |
| 5,250,059 A * | 10/1993 | Andreas et al. .................. 604/22 |
| 5,270,086 A | 12/1993 | Hamlin |
| 5,277,199 A | 1/1994 | DeBois et al. |
| 5,290,306 A | 3/1994 | Trotta et al. |
| 5,300,025 A | 4/1994 | Wantink |
| 5,304,134 A | 4/1994 | Kraus et al. |
| 5,312,430 A | 5/1994 | Rosenbluth et al. |
| 5,318,032 A | 6/1994 | LonsbuTY et al. |
| 5,318,526 A | 6/1994 | Cohen |
| 5,342,386 A | 8/1994 | Trotta |
| 5,358,486 A | 10/1994 | Saab |
| 5,364,357 A | 11/1994 | Aase |
| 5,378,238 A | 1/1995 | Peters et al. |
| 5,395,336 A | 3/1995 | Barclay et al. |
| 5,425,712 A | 6/1995 | Goodin |
| 5,447,497 A | 9/1995 | Sogard et al. |
| 5,451,233 A | 9/1995 | Yock |
| 5,454,789 A | 10/1995 | Burns et al. |
| 5,470,315 A | 11/1995 | Adams |
| 5,476,477 A | 12/1995 | Burns |
| 5,478,320 A | 12/1995 | Trotta |
| 5,484,409 A | 1/1996 | Atkinson et al. |
| 5,490,837 A | 2/1996 | Blaeser et al. |
| 5,496,275 A | 3/1996 | Sirhan et al. |
| 5,499,980 A | 3/1996 | Euteneuer |
| 5,512,051 A | 4/1996 | Wang et al. |
| 5,526,823 A | 6/1996 | Wheeler et al. |
| 5,538,513 A | 7/1996 | Okajima |
| 5,545,134 A | 8/1996 | Hilaire et al. |
| 5,549,552 A | 8/1996 | Peters et al. |
| 5,554,121 A | 9/1996 | Ainsworth et al. |
| 5,556,383 A | 9/1996 | Wang et al. |
| 5,569,195 A | 10/1996 | Saab |
| 5,587,125 A | 12/1996 | Roychowdhury |
| 5,599,326 A | 2/1997 | Carter |
| 5,613,979 A | 3/1997 | Trotta et al. |
| 5,620,649 A | 4/1997 | Trotta |
| 5,622,665 A | 4/1997 | Wang |
| 5,632,760 A | 5/1997 | Sheiban et al. |
| 5,643,209 A | 7/1997 | Fugoso et al. |
| 5,658,264 A | 8/1997 | Samson |
| 5,690,613 A | 11/1997 | Verbeek |
| 5,728,063 A | 3/1998 | Preissman et al. |
| 5,743,874 A | 4/1998 | Fischell et al. |
| 5,743,875 A | 4/1998 | Sirhan et al. |
| 5,749,849 A | 5/1998 | Engelson |
| 5,755,690 A | 5/1998 | Saab et al. |
| 5,759,173 A | 6/1998 | Preissmann et al. |
| 5,766,151 A | 6/1998 | Valley et al. |
| 5,769,817 A | 6/1998 | Burgmeier |
| 5,769,819 A | 6/1998 | Schwab et al. |
| 5,775,327 A | 7/1998 | Randolph et al. |
| 5,779,731 A | 7/1998 | Leavitt |
| 5,782,811 A | 7/1998 | Samson et al. |
| 5,791,036 A | 8/1998 | Goodin et al. |
| 5,792,124 A | 8/1998 | Horrigan et al. |
| 5,792,144 A | 8/1998 | Fischell et al. |
| 5,795,325 A | 8/1998 | Valley et al. |
| 5,795,341 A | 8/1998 | Samson |
| 5,797,887 A | 8/1998 | Rosen et al. |
| 5,814,016 A | 9/1998 | Valley et al. |
| 5,820,594 A | 10/1998 | Fontirroche et al. |
| 5,833,657 A | 11/1998 | Reinhardt et al. |
| 5,879,369 A | 3/1999 | Ishida |
| 5,879,499 A | 3/1999 | Corvi |
| 5,902,290 A | 5/1999 | Peacock et al. |
| 5,908,406 A | 6/1999 | Ostapchenko et al. |
| 5,911,715 A | 6/1999 | Berg et al. |
| 5,916,193 A | 6/1999 | Stevens et al. |
| 5,947,939 A | 9/1999 | Mortier et al. |
| 5,964,778 A | 10/1999 | Fugoso et al. |
| 6,004,289 A | 12/1999 | Saab |
| 6,004,339 A | 12/1999 | Wijay |
| 6,010,521 A | 1/2000 | Lee et al. |
| 6,021,340 A | 2/2000 | Randolph et al. |
| 6,024,693 A | 2/2000 | Schock et al. |
| 6,024,722 A | 2/2000 | Rau et al. |
| 6,027,510 A | 2/2000 | Alt |
| 6,036,670 A | 3/2000 | Wijeratne et al. |
| 6,056,719 A | 5/2000 | Mickley |
| 6,059,751 A | 5/2000 | Ostapchenko et al. |
| 6,059,770 A | 5/2000 | Peacock et al. |
| 6,071,266 A | 6/2000 | Kelley |
| 6,086,556 A | 7/2000 | Hamilton et al. |
| 6,102,890 A | 8/2000 | Stivland et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,165,166 A | 12/2000 | Samuelson et al. |
| 6,165,195 A | 12/2000 | Wilson et al. |
| 6,168,588 B1 | 1/2001 | Wilson |
| 6,171,275 B1 | 1/2001 | Webster, Jr. et al. |
| 6,171,278 B1 | 1/2001 | Wang et al. |
| 6,179,810 B1 | 1/2001 | Wantink et al. |
| 6,179,856 B1 | 1/2001 | Barbere |
| 6,193,686 B1 | 2/2001 | Estrada et al. |
| 6,197,015 B1 | 3/2001 | Wilson |
| 6,210,396 B1 | 4/2001 | MacDonald et al. |
| 6,217,547 B1 | 4/2001 | Lee |
| 6,217,565 B1 | 4/2001 | Cohen |
| 6,242,063 B1 | 6/2001 | Ferrera et al. |
| 6,245,053 B1 | 6/2001 | Benjamin |
| 6,251,093 B1 | 6/2001 | Valley et al. |
| 6,264,683 B1 | 7/2001 | Stack et al. |
| 6,265,016 B1 | 7/2001 | Hostettler et al. |
| 6,306,097 B1 | 10/2001 | Park et al. |
| 6,306,124 B1 | 10/2001 | Jones et al. |
| 6,308,342 B1 | 10/2001 | Qi |
| 6,358,227 B1 | 3/2002 | Ferrera et al. |
| 6,364,894 B1 | 4/2002 | Healy et al. |
| 6,416,494 B1 | 7/2002 | Wilkins |
| 6,482,348 B1 | 11/2002 | Wang et al. |
| 6,495,090 B1 | 12/2002 | Wilkins et al. |
| 6,495,127 B1 | 12/2002 | Wallace et al. |
| 6,500,148 B1 | 12/2002 | Pinchuk et al. |
| 6,508,784 B1 | 1/2003 | Shu |
| 6,575,934 B2 | 6/2003 | Duchamp |
| 6,575,958 B1 | 6/2003 | Happ et al. |
| 6,579,259 B2 | 6/2003 | Stevens et al. |
| 6,585,687 B1 | 7/2003 | Shkolnik |
| 6,585,688 B2 | 7/2003 | Ferrera et al. |
| 6,589,207 B1 | 7/2003 | El-Nounou |
| 6,589,226 B1 | 7/2003 | Owens |
| 6,620,127 B2 | 9/2003 | Lee et al. |
| 6,620,128 B1 | 9/2003 | Simhambhatla |
| 6,626,889 B1 | 9/2003 | Simpson et al. |
| 6,629,961 B1 | 10/2003 | Israelsson et al. |
| 6,645,422 B2 | 11/2003 | Jung, Jr. et al. |
| 6,663,614 B1 | 12/2003 | Carter |
| 6,673,291 B1 | 1/2004 | Field et al. |
| 6,673,302 B2 | 1/2004 | Wang et al. |
| 6,695,809 B1 | 2/2004 | Lee |
| 6,702,802 B1 | 3/2004 | Hancock et al. |
| 6,718,211 B2 | 4/2004 | Smits |
| 6,733,487 B2 | 5/2004 | Keith et al. |
| 6,756,094 B1 | 6/2004 | Wang et al. |
| 6,777,644 B2 | 8/2004 | Peacock et al. |
| 6,793,647 B1 | 9/2004 | Cryer et al. |
| 6,796,958 B2 | 9/2004 | Chen et al. |
| 6,796,960 B2 | 9/2004 | Cioanta et al. |
| 6,835,189 B2 | 12/2004 | Musbach et al. |
| 6,837,890 B1 | 1/2005 | Chludzinski et al. |
| 6,863,678 B2 | 3/2005 | Lee et al. |
| 6,875,197 B1 | 4/2005 | Simhambhatia et al. |
| 6,887,219 B2 * | 5/2005 | Wantink .................. 604/103.04 |
| 6,890,395 B2 | 5/2005 | Simhambhatia et al. |
| 6,893,456 B2 | 5/2005 | Lumauig |

| | | |
|---|---|---|
| 6,911,038 B2 | 6/2005 | Mertens et al. |
| 6,913,600 B2 | 7/2005 | Valley et al. |
| 6,918,920 B1 | 7/2005 | Wang et al. |
| 6,946,092 B1 | 9/2005 | Bertolino et al. |
| 6,951,555 B1 | 10/2005 | Suresh et al. |
| 6,951,675 B2 | 10/2005 | Chin et al. |
| 6,979,342 B2 | 12/2005 | Lee et al. |
| 7,026,026 B2 | 4/2006 | Ferrera et al. |
| 7,029,732 B2 | 4/2006 | Wang et al. |
| 7,037,291 B2 | 5/2006 | Lee et al. |
| 7,037,295 B2 | 5/2006 | Tiernan et al. |
| 7,074,206 B2 | 7/2006 | Lee et al. |
| 7,108,877 B2 | 9/2006 | Blair et al. |
| 7,112,357 B2 | 9/2006 | Miller et al. |
| 7,141,059 B2 | 11/2006 | Duchamp et al. |
| 7,147,817 B1 | 12/2006 | Lim et al. |
| 7,163,523 B2 | 1/2007 | Devens, Jr. et al. |
| 7,195,638 B1 | 3/2007 | Sridharan |
| 7,273,485 B2 | 9/2007 | Simpson et al. |
| 7,335,185 B2 | 2/2008 | Tang et al. |
| 7,341,571 B1 | 3/2008 | Harris et al. |
| 7,556,634 B2 | 7/2009 | Lee et al. |
| 7,662,130 B2 | 2/2010 | Lee et al. |
| 7,833,193 B2 | 11/2010 | Lee et al. |
| 7,906,066 B2 * | 3/2011 | Wilson et al. ............... 264/532 |
| 7,947,059 B2 * | 5/2011 | Chin et al. ............... 606/192 |
| 8,052,638 B2 | 11/2011 | Lee et al. |
| 8,070,719 B2 | 12/2011 | Lee et al. |
| 2001/0001812 A1 | 5/2001 | Valley et al. |
| 2001/0029362 A1 * | 10/2001 | Sirhan et al. ............... 604/524 |
| 2001/0037085 A1 | 11/2001 | Keith et al. |
| 2002/0018866 A1 | 2/2002 | Lee et al. |
| 2002/0165523 A1 * | 11/2002 | Chin et al. ............... 604/523 |
| 2003/0009151 A1 | 1/2003 | Wang |
| 2003/0032920 A1 | 2/2003 | Wantik |
| 2003/0055447 A1 | 3/2003 | Lee et al. |
| 2003/0105426 A1 | 6/2003 | Jorgensen |
| 2003/0139762 A1 | 7/2003 | Lee |
| 2004/0059291 A1 | 3/2004 | McDonnell et al. |
| 2004/0059292 A1 | 3/2004 | Hisamatsu et al. |
| 2004/0064130 A1 | 4/2004 | Carter |
| 2004/0068240 A1 | 4/2004 | Goodin et al. |
| 2004/0097892 A1 | 5/2004 | Evans et al. |
| 2004/0131808 A1 | 7/2004 | Schoenle et al. |
| 2004/0167441 A1 | 8/2004 | Reynolds et al. |
| 2004/0170782 A1 | 9/2004 | Wang et al. |
| 2004/0173935 A1 | 9/2004 | Lim et al. |
| 2004/0181206 A1 | 9/2004 | Chiu et al. |
| 2004/0191443 A1 | 9/2004 | Hamlin |
| 2004/0215141 A1 | 10/2004 | Clarke et al. |
| 2004/0267195 A1 | 12/2004 | Currlin |
| 2004/0267280 A1 | 12/2004 | Nishide et al. |
| 2005/0015048 A1 | 1/2005 | Chiu et al. |
| 2005/0043679 A1 | 2/2005 | Devens et al. |
| 2005/0124976 A1 | 6/2005 | Devens, Jr. et al. |
| 2005/0131445 A1 | 6/2005 | Holman et al. |
| 2005/0148997 A1 | 7/2005 | Valley et al. |
| 2005/0154414 A1 | 7/2005 | Perreault et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0277878 A1 | 12/2005 | Lee |
| 2006/0008606 A1 * | 1/2006 | Horn et al. ............... 428/36.1 |
| 2006/0136032 A1 * | 6/2006 | Legarda et al. ............ 604/103.06 |
| 2006/0165926 A1 | 7/2006 | Weber |
| 2006/0175739 A1 | 8/2006 | Hession et al. |
| 2006/0282041 A1 | 12/2006 | Melsheimer et al. |
| 2007/0060863 A1 | 3/2007 | Goeken et al. |
| 2007/0142771 A1 | 6/2007 | Durcan |
| 2007/0167973 A1 | 7/2007 | Stupecky et al. |
| 2007/0191813 A1 | 8/2007 | Chen |
| 2007/0240817 A1 | 10/2007 | Strong et al. |
| 2008/0045895 A1 | 2/2008 | Simpson et al. |
| 2008/0065188 A1 | 3/2008 | Pallazza |
| 2008/0262470 A1 | 10/2008 | Lee et al. |
| 2009/0005754 A1 | 1/2009 | Soetermans |
| 2009/0156998 A1 | 6/2009 | Arana et al. |
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0130925 A1 | 5/2010 | Haslinger et al. |
| 2011/0315301 A1 | 12/2011 | Simpson et al. |
| 2012/0065586 A1 | 3/2012 | Lee et al. |
| 2012/0143129 A1 | 6/2012 | Simpson et al. |

FOREIGN PATENT DOCUMENTS

| | | |
|---|---|---|
| EP | 0420488 | 3/1991 |
| EP | 0737487 | 10/1996 |
| EP | 0821979 | 2/1998 |
| EP | 0904795 | 3/1999 |
| EP | 0931558 | 7/1999 |
| EP | 0962227 | 8/1999 |
| EP | 1 103 280 A | 5/2001 |
| EP | 1 287 846 A | 3/2003 |
| JP | 10-290837 | 11/1998 |
| JP | 2001-353225 | 12/2001 |
| JP | 2005-167638 | 6/2005 |
| WO | WO/89/02763 | 4/1989 |
| WO | WO 93/20882 | 10/1993 |
| WO | WO 95/18647 | 7/1995 |
| WO | WO 96/03175 | 2/1996 |
| WO | WO 96/34646 | 11/1996 |
| WO | WO 97/26027 | 7/1997 |
| WO | WO 99/13924 | 3/1999 |
| WO | WO 01/34240 | 5/2001 |
| WO | WO 01/34240 A2 | 5/2001 |
| WO | WO 0151115 | 7/2001 |
| WO | WO 01/89621 | 11/2001 |
| WO | WO 02/36196 | 5/2002 |
| WO | 03004248 A1 | 1/2003 |
| WO | WO 2005021083 | 3/2005 |
| WO | WO 2006126311 | 11/2006 |
| WO | WO/2007/054364 | 5/2007 |
| WO | WO/2007/146572 | 12/2007 |

OTHER PUBLICATIONS

U.S. Appl. No. 11/480,143, filed Jul. 1, 2008—Response to Election/Restriction.
U.S. Appl. No. 11/480,143, filed Oct. 17, 2008—Requirement for Restriction/Election.
U.S. Appl. No. 11/480,143, filed Oct. 28, 2008—Response to Election/Restriction.
U.S. Appl. No. 11/480,143, filed Jan. 27, 2009—Non-Final Office Action.
U.S. Appl. No. 11/480,143, filed May 27, 2009—Response to Non-Final Office Action.
U.S. Appl. No. 11/480,143, filed Aug. 18, 2009—Final Office Action.
U.S. Appl. No. 11/480,143, filed Jan. 15, 2010—Amendment After Final Rejection.
U.S. Appl. No. 11/480,143, filed Feb. 4, 2010—Advisory Action.
U.S. Appl. No. 11/480,143, filed Feb. 18, 2010—Request for Continued Examination.
U.S. Appl. No. 11/480,143, filed Apr. 22, 2010—Non-Final Office Action.
U.S. Appl. No. 11/480,143, filed Aug. 23, 2010—Response to Non-Final Office Action.
U.S. Appl. No. 10/392,657, filed Sep. 5, 2007, Issue Notification.
U.S. Appl. No. 10/392,657, filed Aug. 22, 2007, Issue Fee Payment.
U.S. Appl. No. 10/392,657, filed May 31, 2007, Notice of Allowance.
U.S. Appl. No. 10/392,657, filed Feb. 26, 2007, Response to Final Office Action.
U.S. Appl. No. 10/392,657, filed Jan. 5, 2007, Final Office Action.
U.S. Appl. No. 10/392,657, filed Sep. 29, 2006, Response to Non-Final Office Action.
U.S. Appl. No. 10/392,657, filed Jul. 13, 2006, Non-Final Office Action.
U.S. Appl. No. 10/392,657, filed May 1, 2006, Response to Restriction Requirement.
U.S. Appl. No. 10/392,657, filed Mar. 27, 2006, Restriction Requirement.
U.S. Appl. No. 11/196,134, filed Jan. 27, 2010, Issue Notification.
U.S. Appl. No. 11/196,134, filed Dec. 29, 2009, Issue Fee Payment.
U.S. Appl. No. 11/196,134, filed Sep. 30, 2009, Notice of Allowance.

U.S. Appl. No. 11/196,134, filed Sep. 10, 2009, Response to Final Office Action.
U.S. Appl. No. 11/196,134, filed Jun. 10, 2009, Final Office Action.
U.S. Appl. No. 11/196,134, filed Mar. 24, 2009, Response to Non-Final Office Action.
U.S. Appl. No. 11/196,134, filed Dec. 24, 2008, Non-Final Office Action.
U.S. Appl. No. 11/844,117, filed Aug. 17, 2010, Final Office Action.
U.S. Appl. No. 11/844,117, filed Jun. 30, 2010, Response to Non-Final Office Action.
U.S. Appl. No. 11/844,117, filed Jun. 23, 2010, Notice of Non-Compliant Amendment.
U.S. Appl. No. 11/844,117, filed Jun. 17, 2010, Response to Non-Final Office Action.
U.S. Appl. No. 11/844,117, filed Mar. 17, 2010, Non-Final Office Action.
U.S. Appl. No. 11/844,117, filed Jan. 5, 2010, Response to Restriction Requirement.
U.S. Appl. No. 11/844,117, filed Oct. 13, 2009, Restriction Requirement.
U.S. Appl. No. 11/958,106, filed Jun. 17, 2010, Response to Final Office Action.
U.S. Appl. No. 11/958,106, filed Mar. 17, 2010, Final Office Action.
U.S. Appl. No. 11/958,106, filed Jan. 8, 2010, Response to Non-Final Office Action.
U.S. Appl. No. 11/958,106, filed Jul. 8, 2009, Non-Final Office Action.
U.S. Appl. No. 11/038,971, filed Jun. 17, 2009, Issue Notification.
U.S. Appl. No. 11/038,971, filed May 29, 2009, Issue Fee Payment.
U.S. Appl. No. 11/038,971, filed Mar. 13, 2009, Notice of Allowance.
U.S. Appl. No. 11/038,971, filed Sep. 19, 2008, Response to Non-Final Office Action.
U.S. Appl. No. 11/038,971, filed Jul. 29, 2008, Non-Final Office Action.
U.S. Appl. No. 11/038,971, filed Feb. 28, 2008, Response to Non-Final Office Action.
U.S. Appl. No. 11/038,971, filed Nov. 28, 2007, Non-Final Office Action.
U.S. Appl. No. 11/038,971, filed Sep. 18, 2007, Response to Non-Final Office Action.
U.S. Appl. No. 11/038,971, filed Jun. 28, 2007, Non-Final Office Action.
U.S. Appl. No. 11/038,971, filed Apr. 12, 2007, Response to Final Office Action.
U.S. Appl. No. 11/038,971, filed Feb. 16, 2007, Final Office Action.
U.S. Appl. No. 11/038,971, filed Dec. 8, 2006, Terminal Disclaimer.
U.S. Appl. No. 11/038,971, filed Nov. 13, 2006, Response to Non-Final Office Action.
U.S. Appl. No. 11/038,971, filed Sep. 21, 2006, Non-Final Office Action.
U.S. Appl. No. 11/480,143, Notice of Allowance mailed Nov. 18, 2010.
U.S. Appl. No. 12/478,929, Response to Non-Final Office Action filed Jul. 9 2010 mailed Dec. 9, 2010.
U.S. Appl. No. 11/844,117, Response to Final Office Action filed Aug. 17, 2010 mailed Nov. 17, 2010.
U.S. Appl. No. 11/844,117, Non-Final Rejection mailed Nov. 23, 2010.
U.S. Appl. No. 10/392,657, Notice of Allowance mailed Apr. 14, 2004.
U.S. Appl. No. 10/392,657, Response to Non-Final Office Action filed Nov. 21, 2003 filed Feb. 20, 2004.
U.S. Appl. No. 10/392,657, Non-Final Office Action filed Nov. 21, 2003.
U.S. Appl. No. 12/478,929, Jun. 22, 2012, Non-Final Office Action.
U.S. Appl. No. 13/562,810, filed Jul. 31, 2012.
U.S. Appl. No. 11/958,106, Aug. 1, 2012, Non-Final Office Action.
International Search Report for PCT/US2007/071873, dated Apr. 14, 2008.
International Search Report for PCT/US2008/086270, dated Jun. 3, 2009.
U.S. Appl. No. 12/478,929, filed Jul. 9, 2010—Non-Final Office Action.
U.S. Appl. No. 13/398,178, filed Feb. 16, 2012.
U.S. Appl. No. 11/958,106, filed Dec. 17, 2007, Arana et al.
U.S. Appl. No. 12/324,425, filed Nov. 26, 2008, Lee.
U.S. Appl. No. 12/479,700, filed Jun. 5, 2009, Lee et al.
U.S. Appl. No. 13/240,453, filed Sep. 22, 2011, Lee et al.
U.S. Appl. No. 09/957,526, filed Sep. 19, 2001, Lee et al.
U.S. Appl. No. 12/477,695, filed Jun. 3, 2009, Lee et al.
U.S. Appl. No. 10/932,697, filed Mar. 20, 2003, Simpson et al.
U.S. Appl. No. 13/224,917, filed Sep. 2, 2011, Simpson et al.
U.S. Appl. No. 10/010,212, filed Dec. 4, 2001, Lee et al.
U.S. Appl. No. 12/687,265, filed Jan. 14, 2010, Lee.
U.S. Appl. No. 11/763,623, Aug. 24, 2010 Amendment and Request for Continued Examination (RCE).
U.S. Appl. No. 11/763,623, May 24, 2010 Notice of Appeal.
U.S. Appl. No. 11/763,623, Feb. 23, 2010 Final Office Action.
U.S. Appl. No. 11/763,623, Jan. 15, 2010 Response to Non-Final Office Action.
U.S. Appl. No. 11/763,623, Oct. 15, 2009 Non-Final Office Action.
U.S. Appl. No. 11/763,623, Jul. 20, 2009 Amendment and Request for Continued Examination (RCE).
U.S. Appl. No. 11/763,623, Mar. 20, 2009 Final Office Action.
U.S. Appl. No. 11/763,623, Mar. 3, 2009 Response to Non-Final Office Action.
U.S. Appl. No. 11/763,623, Dec. 3, 2008 Non-Final Office Action.
U.S. Appl. No. 11/958,106, May 29, 2012 Response to Non-Compliant.
U.S. Appl. No. 11/958,106, May 17, 2012 Notice of Non-Compliant.
U.S. Appl. No. 11/958,106, May 7, 2012 Response to Non-Final Office Action.
U.S. Appl. No. 11/958,106, Jan. 6, 2012 Non-Final Office Action.
U.S. Appl. No. 11/958,106, Jul. 8, 2009 Non-Final Office Action.
U.S. Appl. No. 12/324,425, Sep. 22, 2011 Issue Fee payment.
U.S. Appl. No. 12/324,425, Aug. 31, 2011 Notice of Allowance.
U.S. Appl. No. 12/324,425, Jun. 6, 2011 Response to Non-Final Office Action.
U.S. Appl. No. 12/324,425, Mar. 4, 2011 Non-Final Office Action.
U.S. Appl. No. 12/479,700, Sep. 22, 2011 Issue Fee payment.
U.S. Appl. No. 12/479,700, Aug. 22, 2011 Notice of Allowance.
U.S. Appl. No. 12/479,700, May 20, 2011 Response to Interview Summary.
U.S. Appl. No. 12/479,700, May 13, 2011 Examiner Interview Summary.
U.S. Appl. No. 12/479,700, Apr. 27, 2011 Response to Non-Final Office Action.
U.S. Appl. No. 12/479,700, Oct. 27, 2010 Non-Final Office Action.
U.S. Appl. No. 12/478,929, Jul. 18, 2011 Request for Continued Examination (RCE).
U.S. Appl. No. 12/478,929, Jul. 13, 2011 Advisory Action.
U.S. Appl. No. 12/478,929, Jun. 6, 2011 Response to Final Office Action.
U.S. Appl. No. 12/478,929, Mar. 4, 2011 Final Office Action.
U.S. Appl. No. 09/957,526, Jan. 24, 2005 Issue Fee payment.
U.S. Appl. No. 09/957,526, Nov. 4, 2004 Notice of Allowance.
U.S. Appl. No. 09/957,526, Sep. 21, 2004 Response to Non-Final Office Action.
U.S. Appl. No. 09/957,526, Jul. 1, 2004 Non-Final Office Action.
U.S. Appl. No. 09/957,526, Apr. 22, 2004 Amendment and Request for Continued Examination (RCE).
U.S. Appl. No. 09/957,526, Feb. 17, 2004 Final Office Action.
U.S. Appl. No. 09/957,526, Nov. 26, 2003 Response to Non-Final Office Action.
U.S. Appl. No. 09/957,526, Jun. 23, 2003 Non-Final Office Action.
U.S. Appl. No. 12/477,695, Apr. 16, 2012 Response to Non-Final Office Action.
U.S. Appl. No. 12/477,695, Dec. 16, 2011 Non-Final Office Action.
U.S. Appl. No. 10/392,697, Aug. 22, 2007 Issue Fee payment.
U.S. Appl. No. 10/392,697, May 31, 2007 Notice of Allowance.
U.S. Appl. No. 10/392,697, Feb. 26, 2007 Amendment and Request for Continued Examination (RCE).
U.S. Appl. No. 10/392,697, Jan. 5, 2007 Final Office Action.
U.S. Appl. No. 10/392,697, Sep. 29, 2006 Response to Non-Final Office Action.
U.S. Appl. No. 10/392,697, Jul. 13, 2006 Non-Final Office Action.

U.S. Appl. No. 11/844,117, Aug. 2, 2011 Issue Fee payment.
U.S. Appl. No. 11/844,117, Jun. 15, 2011 Notice of Allowance.
U.S. Appl. No. 11/844,117, Mar. 23, 2011 Response to Non-Final Office Action.
U.S. Appl. No. 11/844,117, Nov. 23, 2010 Non-Final Office Action.
U.S. Appl. No. 11/844,117, Nov. 17, 2010 Amendment and Request for Continued Examination (RCE).
U.S. Appl. No. 10/010,212, Mar. 6, 2006 Issue Fee payment.
U.S. Appl. No. 10/010,212, Feb. 9, 2006 Notice of Allowance.
U.S. Appl. No. 10/010,212, Dec. 27, 2005 Response to Final Office Action.
U.S. Appl. No. 10/010,212, Oct. 19, 2005 Final Office Action.
U.S. Appl. No. 10/010,212, Aug. 4, 2005 Response to Non-Final Office Action.
U.S. Appl. No. 10/010,212, May 6, 2005 Non-Final Office Action.
U.S. Appl. No. 10/010,212, Feb. 4, 2005 Amendment and Request for Continued Examination (RCE).
U.S. Appl. No. 10/010,212, Dec. 2, 2004 Final Office Action.
U.S. Appl. No. 10/010,212, Aug. 9, 2004 Response to Non-Final Office Action.
U.S. Appl. No. 10/010,212, Jun. 16, 2004 Non-Final Office Action.
U.S. Appl. No. 10/010,212, Mar. 22, 2004 Response to Non-Final Office Action.
U.S. Appl. No. 10/010,212, Dec. 31, 2003 Non-Final Office Action.
U.S. Appl. No. 10/010,212, Oct. 14, 2003 Amendment and Request for Continued Examination (RCE).
U.S. Appl. No. 10/010,212, Jul. 7, 2003 Final Office Action.
U.S. Appl. No. 10/010,212, Apr. 18, 2003 Response to Non-Final Office Action.
U.S. Appl. No. 10/010,212, Jan. 15, 2003 Non-Final Office Action.
U.S. Appl. No. 12/687,265, Oct. 14, 2010 Issue Fee payment.
U.S. Appl. No. 12/687,265, Aug. 5, 2010 Notice of Allowance.
U.S. Appl. No. 11/958,106, Oct. 23, 2012 Response to Non-Final Office Action.
U.S. Appl. No. 13/398,178, Oct. 25, 2012 Notice of Allowance.
U.S. Appl. No. 12/478,929, Sep. 24, 2012 Response to Non-Final Office Action.
U.S. Appl. No. 12/477,695, Oct. 24, 2012 Advisory Action.
U.S. Appl. No. 12/477,695, Oct. 11, 2012 Response to Final Office Action.
U.S. Appl. No. 12/477,695, Aug. 15, 2012 Final Office Action.
U.S. Appl. No. 13/224,917, Oct. 12, 2012 Non-Final Office Action.

* cited by examiner

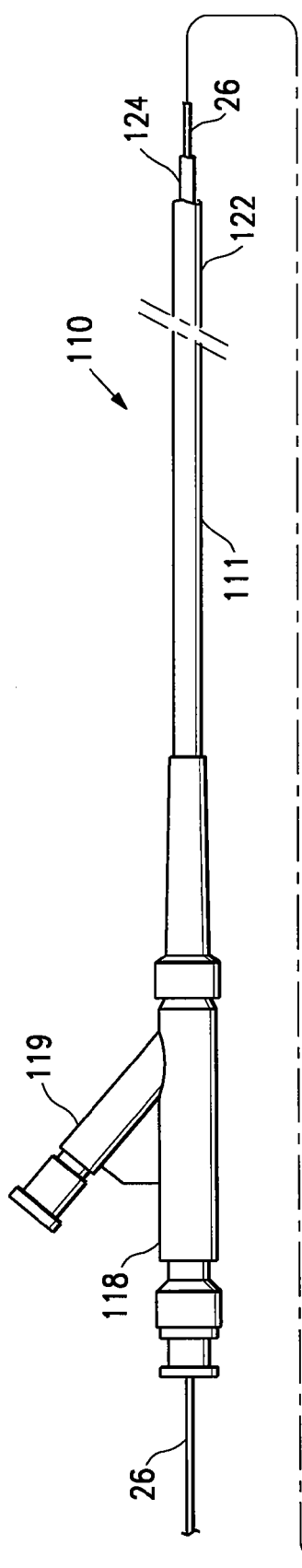
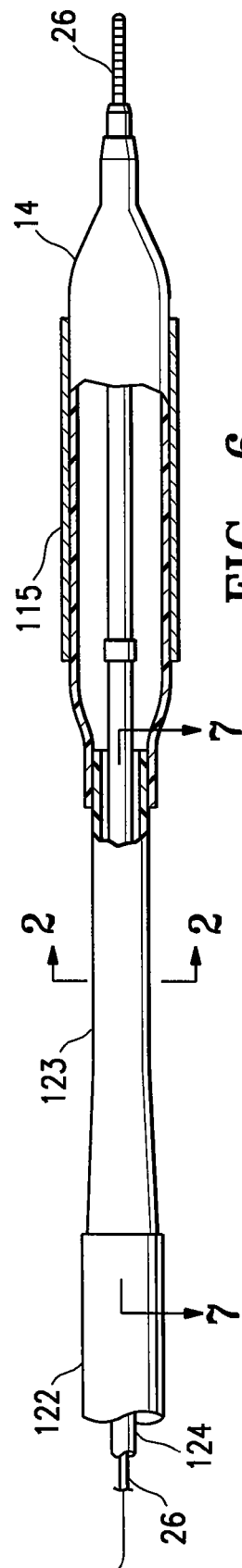
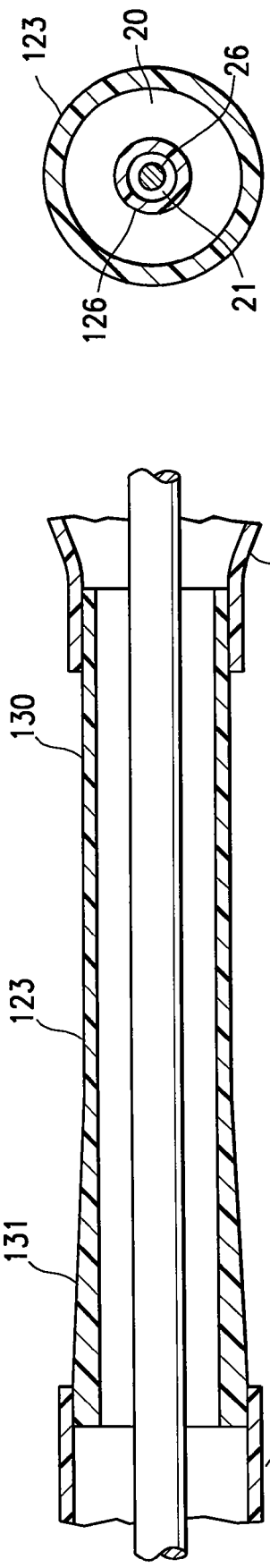
FIG. 6
FIG. 7
FIG. 8

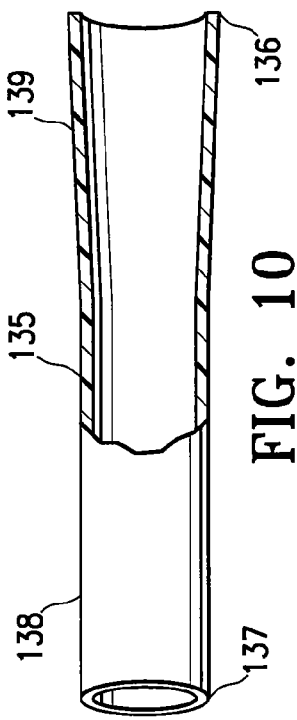
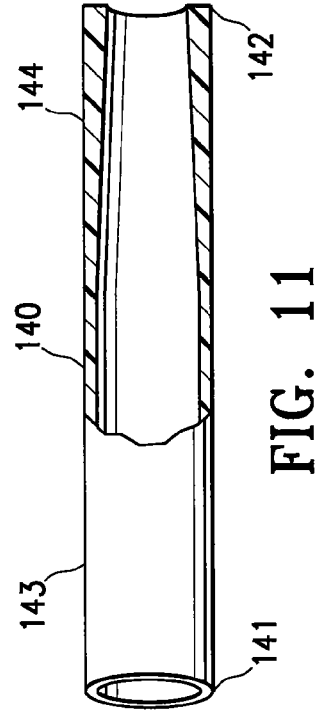
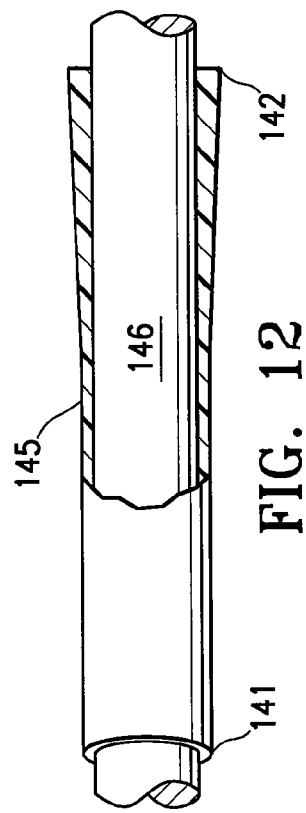
FIG. 10
FIG. 11
FIG. 12
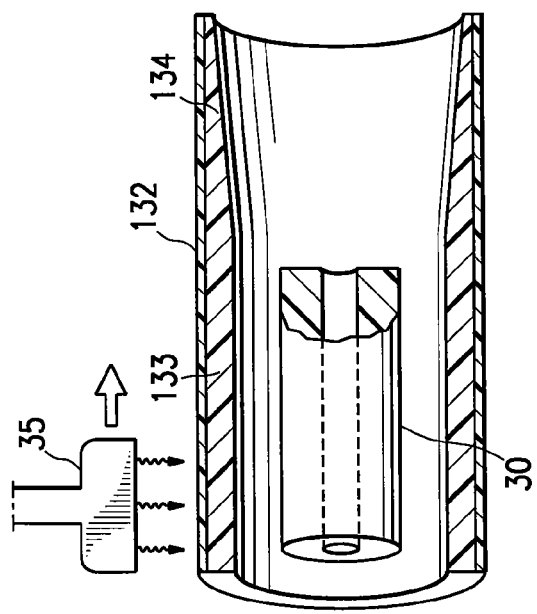
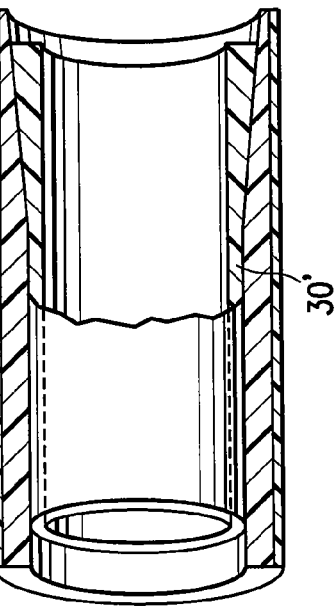
FIG. 9A
FIG. 9B

BALLOON CATHETER TAPERED SHAFT HAVING HIGH STRENGTH AND FLEXIBILITY AND METHOD OF MAKING SAME

CROSS-REFERENCES TO RELATED APPLICATIONS

This application is a continuation-in-part of application Ser. No. 11/480,143, filed Jun. 30, 2006, now U.S. Pat. No. 7,906,066, incorporated by reference herein in its entirety.

FIELD OF THE INVENTION

This invention relates generally to medical devices, and particularly to intracorporeal devices for therapeutic or diagnostic uses, such as balloon catheters.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter shafts, strength, stiffness and flexibility of various sections of the catheter shaft are specifically tailored to provide the desired catheter performance. However, one difficulty has been optimizing the often competing characteristics of strength and flexibility of the catheter shaft.

Accordingly, it would be a significant advance to provide a catheter having a catheter shaft with an improved combination of characteristics such as strength, flexibility and ease of manufacture. This invention satisfies these and other needs.

SUMMARY OF THE INVENTION

This invention is directed to a catheter having an elongated shaft with a tubular member which forms at least a portion of the shaft and which is formed of a biaxially oriented thermoplastic polymeric material. One aspect of the invention is directed to a method of forming the catheter shaft by radially and longitudinally expanding the tubular member to biaxially orient the polymeric material. Additionally, one aspect of the invention is directed to forming a taper along at least a section of the biaxially oriented tubular member to provide a bending stiffness transition. A catheter of the invention preferably has an improved combination of low bending stiffness, high rupture pressure, and high tensile strength, for improved catheter performance.

A method of making a catheter shaft of the invention generally comprises radially and longitudinally expanding an extruded tube, which results in an expanded tubular member having a higher rupture pressure and tensile strength than a tube extruded directly to the same final dimensions (i.e., wall thickness and outer diameter) as the expanded tubular member. It is believed that the radial and longitudinal expansion circumferentially and longitudinally orients the polymeric structure within the material. However, the orientation does not significantly increase the bending stiffness of the tubular member. Thus, a relatively low durometer polymer can be selected to minimize bending stiffness in the radially and axially deformed tubular member. The inherently low bending stiffness of the low durometer polymer provides a longitudinally flexible shaft tubular member which more readily bends during maneuvering of the catheter within the patient.

In a presently preferred embodiment, the catheter is a balloon catheter generally comprising an elongated shaft having a proximal end, a distal end, an inflation lumen extending therein, and a tubular member which has the inflation lumen therein and which is formed of a biaxially oriented nonporous thermoplastic polymer, and a balloon sealingly secured to a distal shaft section. In one embodiment, the balloon is a relatively high pressure balloon. The biaxially oriented polymer has polymer chains oriented longitudinally along the tubular member for increased tensile strength, and circumferentially around the tubular member for increased rupture pressure. The high tensile strength of the shaft tubular member improves catheter performance by, for example, increasing the ability to safely pull the catheter from within the patient's vessel without tearing apart/damaging the catheter, e.g., during retrieval of the catheter lodged in a calcific lesion.

The balloon has an interior in fluid communication with the inflation lumen, and a rupture pressure which is significantly less than the rupture pressure of the shaft tubular member. As a result, the balloon catheter preferably has a failure mode in which the balloon will rupture before the pressure-containing catheter shaft tubular member, to prevent or minimize vessel injury in the event of a catheter rupture. In one embodiment, the balloon is a relatively high pressure balloon, for example having a rupture pressure of at least about 20 atm or more. The shaft tubular member preferably has a mean rupture strength substantially greater than that of the balloon, so that the distribution of the two rupture pressure ranges have essentially no statistical overlap.

In a method of making a balloon catheter having an elongated shaft and a balloon on a distal shaft section, a thermoplastic polymeric material having a relatively low Shore durometer hardness is melt-extruded to form a tube having a lumen and a first inner and outer diameter which are smaller than the desired final dimensions of a shaft tubular member. The method includes cooling the extruded tube to a temperature less than an elevated temperature of the melt-extrusion, and placing the extruded tube in a lumen of a capture member, and biaxially orienting the polymeric material of the extruded tube within the capture member at an elevated temperature. The tube is biaxially oriented by radially expanding the heated extruded tube with pressurized media in the tube lumen and simultaneously or sequentially axially expanding the extruded tube with a load applied on at least one end of the tube. The expanded tube is thus radially and axially expanded to a second (larger) outer and inner diameter and a second (longer) length. The second outer diameter is generally about equal to the inner diameter of the capture member, and the second inner diameter is preferably at least about 5 times larger than the first inner diameter of the extruded tube. The expanded tube is then cooled to room temperature, to produce the biaxially oriented nonporous thermoplastic polymer tubular member (hereafter, "the biaxially oriented tubular member"), which forms at least a portion of the catheter shaft.

The amount of radial expansion is selected to produce a high degree of circumferential orientation, which results in a correspondingly high rupture pressure for use as a shaft section which contains the inflation lumen therein. Thus, the method includes sealingly securing a balloon to a distal end of the biaxially oriented tubular member, such that the balloon has an interior in fluid communication with the lumen (i.e., the inflation lumen) of the biaxially oriented tubular member during catheter assembly.

By extruding a low durometer thermoplastic material to form a tube having a significantly smaller inner diameter and larger wall thickness than the required shaft tubular member, and then radially and longitudinally expanding the tube, a tubular member is provided which has a low bending stiffness but nonetheless has high rupture pressure and tensile strength. Moreover, the increased rupture pressure is not provided at the expense of other performance characteristics of the catheter. For example, although the rupture pressure of a tubular shaft can be increased by increasing the wall thickness, the corresponding decrease in the shaft inner and/or outer diameter disadvantageously increases the inflation/deflation time and the profile of the shaft.

The Shore durometer hardness of the polymeric material, and the extruded and expanded dimensions of the tubing are selected such that the resulting tubular member preferably has a Gurley bending stiffness value of not greater than about 50 to about 150 mg, a rupture pressure of at least about 25 to about 50 atm, and a tensile break load of at least about 1.0 to about 5.0 lbf. In a presently preferred embodiment, the Shore durometer hardness of the polymeric material is about 63 D, although a polymeric material having a lower or higher Shore durometer hardness can alternatively be used. Polymeric materials found useful in the invention typically have a Shore durometer hardness of about 55 D to about 75 D.

In the design of shafts for balloon catheters, extruded catheter shaft tubing is conventionally resized to a smaller diameter and wall thickness by necking the tubing using a die and mandrel. Unlike such conventional necking procedures which force the tubing through a die and thus primarily elongate the tubing with only a minimal decrease in tubing diameter and/or wall thickness, the catheter shaft tubing of the invention is highly circumferentially oriented by being radially expanded to an inner diameter significantly larger than the original (extruded) inner diameter. In one embodiment, the tubing is radially expanded to substantially the maximum amount possible (based on the polymeric material and extruded tubing dimensions), which results in expanded tubing having minimal radial growth at increasing inner pressures. Consequently, the expanded tubing has an improved controlled failure mode. In the event that the shaft tubing is over-pressurized above the rupture pressure of the shaft tubing, the expanded tubing preferably fails by rupturing with a small longitudinally extending slit and without radially expanding against the vessel wall, which thus prevents or minimizes vessel injury.

In one embodiment, the biaxially oriented tubular member is provided with a wall thickness and/or diameter that tapers along at least a section of the biaxially oriented tubular member, to thereby vary the bending stiffness therealong. In a presently preferred embodiment, the tapered section is formed during the biaxial orientation of the tube by varying an external load applied on at least one end of the extruded tube as a function of a heating nozzle position (i.e., as the heating nozzle traverses along the length of the extruded tube during the biaxial orientation expansion, the external axial load is varied, to vary the amount of axial expansion). The resulting tapered section of the biaxially oriented tubular member can have a variety of different configurations depending on factors such as the amount by which the external load is varied and whether the capture member has a tapered inner diameter. In a presently preferred embodiment, the resulting tapered section of the biaxially oriented tubular member tapers distally to a smaller outer diameter and wall thickness, but has a substantially constant inner diameter. However, a variety of suitable configurations can be used including a tapered section having a tapered inner diameter with or without a tapered outer diameter and wall thickness.

Although discussed herein primarily in terms of a tapering method in which the extruded tube is tapered by varying the external axial load during the biaxial expansion of the tube, the taper can be formed using additional or alternative methods. For example, the internal pressure used to radially expand the extruded tube during the biaxial orientation also exerts an axial force which can expand the tube in the axial direction. Therefore, varying the internal gas pressure during biaxial orientation will change the overall axial load carried by the tube's cross section and thus the total axial stress arising during biaxial orientation. Additionally, the expanded tubular member's dimensions can be modified after the biaxial expansion by radially shrinking the biaxially oriented tubular member onto a mandrel during a heat stabilization process. Depending on the shape (e.g., tapering or nontapering) of the mandrel and the biaxially oriented tubular member prior to the heat stabilization process, this radial shrinking can produce a finished part having a constant or varying inner diameter and/or outer diameter. However, radial and axial shrinkage onto a mandrel after the biaxial orientation produces a greater wall thickening in sections having greater initial clearance between the biaxially oriented tubular member and the mandrel outer diameter. Thus, in one presently preferred embodiment, the amount of shrinkage during the heat stabilization process is minimized, by heat stabilizing the biaxially oriented tubular member on a mandrel having an outer diameter profile which closely matches (i.e., little initial clearance within) the inner diameter of the as-expanded biaxially oriented tubular member.

Although a taper can be produced using various methods, a preferred embodiment produces a relatively large stiffness transition, without sacrificing the desired degree of biaxial orientation, and without a disadvantageous decrease in the inner lumen diameter. In a presently preferred embodiment, the bending stiffness of the tapered biaxially oriented tubular member varies by a factor of about 2 to about 4.5 along the length of the taper. The stiffness transition is typically provided over a relatively long length. However, the biaxially oriented tubular member can be provided with a stiffness transition due to the varying wall thickness and/or diameter which is abrupt (e.g., occurring over about 1 cm), less abrupt (e.g., occurring over a few to many centimeters), or essentially continuous (e.g., occurring over all or a substantial majority of the length of the tubular member). Generally, the tapered biaxially oriented tubular member has at least a section which has a distally tapering wall thickness and/or diameter along a length of at least about 1 cm, or about 2% of the total length of the biaxially oriented tubular member.

The tapered biaxially oriented tubular member can be used in a variety of suitable locations of a variety of catheters, although it is typically a relatively flexible distal section of the catheter shaft, with the tapered section enhancing the stiffness transition from a highly flexible distal end to a substantially more rigid proximal section of the catheter shaft. In a presently preferred embodiment, the stiffness transition of the tapered biaxially oriented tubular member eliminates the need for a separate mid-shaft section secured to the distal end of a stiff proximal section and the proximal end of a flexible distal section of the shaft. The tapered biaxially oriented tubular member thus preferably provides improved catheter deliverability without increasing the number of shaft components or complicating catheter assembly.

The invention provides a catheter shaft tubular member having an improved combination of low bending stiffness, high rupture pressure, and high tensile strength. Preferably, a catheter shaft tubular member of the invention has a low profile and high flexibility such that the catheter has excellent ability to track and to cross tight, tortuous anatomy, while having a high rupture pressure and the ability to maintain inflation lumen integrity during a medical procedure. The high rupture pressure catheter shaft assures that inadvertent over-pressurization will normally result in rupture within the balloon (and most notably even a relatively high rupture pressure balloon) at the treatment site rather than elsewhere in the patient's vasculature. Unlike conventional catheter design in which shaft sections requiring minimized profile and/or maximized lumen size are typically formed of high strength/stiffness materials to allow for the shaft to be formed with thin walls, the catheter shaft section of the invention is formed of a relatively low durometer polymeric material providing a low bending stiffness. Similarly, unlike shaft sections formed with multiple layers or reinforcements to increase the burst pressure/strength of the shaft, the catheter shaft section of the invention has relatively thin walls, for minimizing the shaft profile while maximizing the shaft lumen size, and for minimizing the shaft bending stiffness.

These and other advantages of the invention will become more apparent from the following detailed description and accompanying exemplary drawings.

BRIEF DESCRIPTION OF THE DRAWINGS

FIG. 6 is an elevational view, partially in section, of an over-the-wire stent delivery balloon catheter embodying features of the invention, which has a tapered biaxially oriented tubular member forming a portion of the catheter shaft.

FIG. 7 is a longitudinal cross sectional view of the catheter shaft of FIG. 6, taken along line 7-7.

FIG. 8 is a transverse cross sectional view of the balloon catheter shown in FIG. 6, taken along line 8-8.

FIG. 9a illustrates a method of forming a tapered biaxially oriented tubular member, with an extruded tube shown prior to being radially and longitudinally expanded within a tapered capture tube.

FIG. 9b illustrates the extruded tube of FIG. 9a after being radially and longitudinally expanded in the capture member.

FIG. 10 illustrates a tapered biaxially oriented tubular member having a section with a tapered inner and outer diameter.

FIG. 11 illustrates a tapered biaxially oriented tubular member having a section with a tapered inner diameter, and a uniform outer diameter.

FIG. 12 illustrates the tapered biaxially oriented tubular member of FIG. 11 after being heat stabilized on a uniform diameter mandrel.

DETAILED DESCRIPTION OF THE PREFERRED EMBODIMENTS

Figure 1:
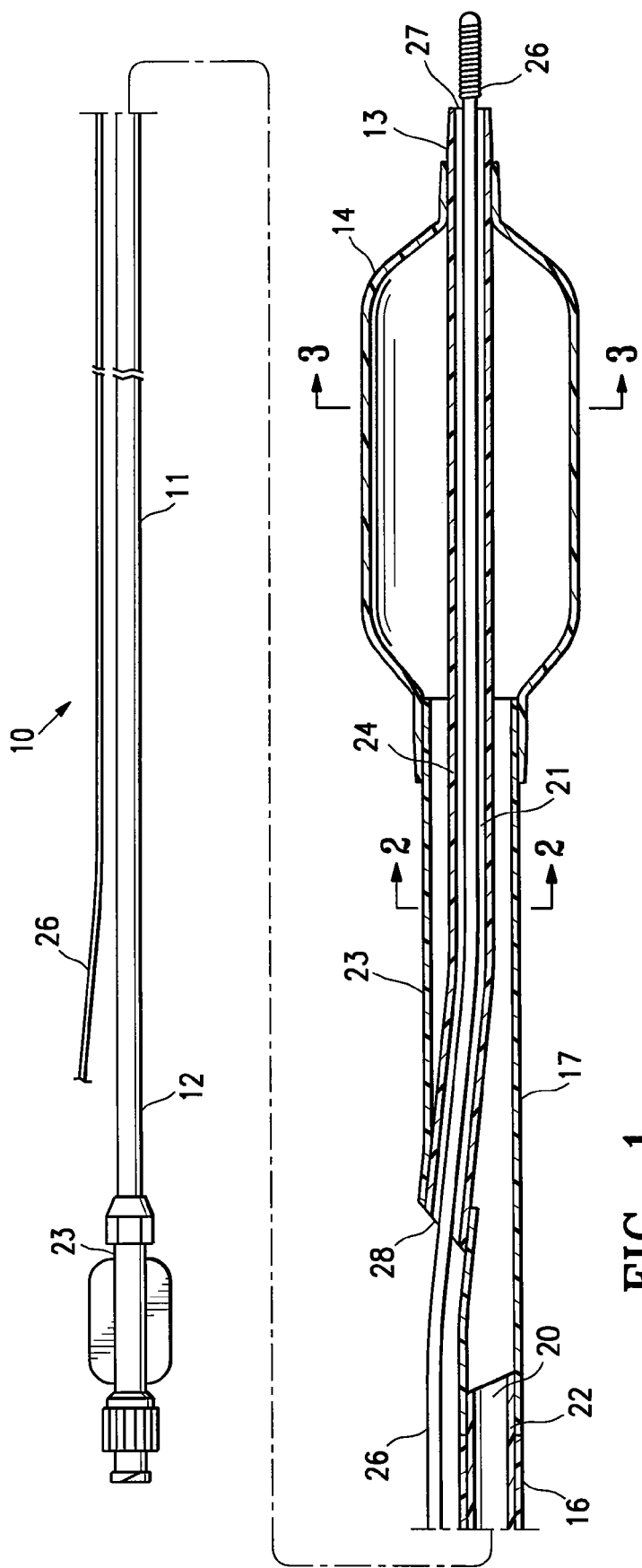
FIG. 1 is an elevational view, partially in section, of a balloon catheter embodying features of the invention.
Figure 3:
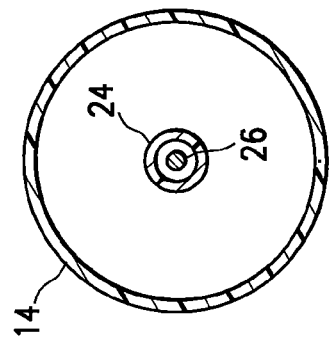
FIGS. 2 and 3 are transverse cross sectional views of the balloon catheter shown in FIG. 1, taken along lines 2-2 and 3-3, respectively.
Figure 2:
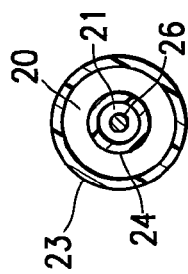

FIG. 1 illustrates a rapid exchange type balloon dilatation catheter 10 embodying features of the invention. Catheter 10 generally comprises an elongated catheter shaft 11 having a proximal end 12, a distal end 13, a proximal shaft section 16, and a distal shaft section 17, and an inflatable balloon 14 on the distal shaft section. The shaft 11 has an inflation lumen 20, and a guidewire receiving lumen 21. An adapter 18 at the proximal end of the catheter provides access to the inflation lumen 20 and is configured for connecting to an inflation fluid source (not shown). The distal end of the catheter may be advanced to a desired region of a patient's body lumen in a conventional manner and balloon 14 inflated to perform a medical procedure such a dilate a stenosis, and catheter 10 withdrawn or repositioned for another procedure. FIG. 1 illustrates the balloon inflated. FIGS. 2 and 3, illustrate transverse cross sections of the catheter of FIG. 1, taken along lines 2-2 and 3-3, respectively.

In the illustrated embodiment, the proximal shaft section 16 comprises a proximal tubular member 22 defining a proximal portion of the inflation lumen 20, and the distal shaft section 17 comprises a distal outer tubular member 23 defining a distal portion of the inflation lumen 20, and an inner tubular member 24 defining the guidewire lumen 21 configured to slidably receive guidewire 26 therein. As a rapid exchange type catheter, the guidewire lumen 21 extends from a distal port 27 at the distal end of the catheter to a proximal port 28 spaced distally from the proximal end of the catheter. The rapid exchange junction at the guidewire proximal port 28 is the transition between the single lumen proximal shaft section and the multilumen distal shaft section in the illustrated embodiment. Similarly, in one embodiment, the guidewire proximal port 28 is located in a midshaft section extending between and connecting the proximal tubular member 22 and the distal outer member 23. The distal shaft section is preferably more flexible than the proximal shaft section, and the proximal tubular member is therefore typically a relatively high stiffness material such as a metal or high durometer polymer. As best illustrated in FIG. 2, the inflation lumen 20 in the distal shaft section is the annular space between the inner surface of the outer tubular member 23 and the outer surface of the inner tubular member 24, although a variety of suitable shaft configurations can alternatively be used including non-coaxial and multi-lumen extrusions.

Balloon 14 is sealingly secured to the shaft such that the balloon interior is in fluid communication with the shaft inflation lumen 20. Specifically, in the illustrated embodiment, the balloon 14 has a proximal skirt section bonded to the distal end of shaft distal outer tubular member 23 and a distal skirt section bonded to the distal end of shaft inner tubular member 24. The balloon 14 is preferably formed of a polymeric material which is compatible with the material forming the outer surface of the shaft, to allow for fusion bonding, although the balloon can alternatively or additionally be adhesively bonded to the shaft. The balloon 14 is preferably a relatively high rupture pressure, non-compliant balloon, which in one embodiment has a rupture pressure of about 20 to about 30 atm, such that the balloon can be inflated in the patient during a procedure at relatively high working pressure of about 18 atm. In one embodiment, the balloon has a rated burst pressure of about 14 to about 25 atm. The rated burst pressure (RBP), calculated from the average rupture pressure, is the pressure at which 99.9% of the balloons can be pressurized to without rupturing, with 95% confidence. Generally, a balloon 14 is inflated in the patient during a procedure at working pressure of about 8 to about 18 atm.

In accordance with the invention, at least a portion of the catheter shaft 11 comprises a tubular member formed of a biaxially oriented thermoplastic polymeric material, which in the illustrated embodiment preferably is the distal outer tubular member 23 (hereafter "the biaxially oriented distal outer tubular member") having the inflation lumen 20 therein. A catheter of the invention can have a biaxially oriented tubular member alternatively or additionally forming other sections of the catheter shaft including proximal and midshaft sections. However, unlike the proximal shaft section which is typically formed of a relatively high bending stiffness material to provide sufficient push (force transmission) for advancing the catheter in the patient's vasculature, the distal shaft section preferably has tubular members with a low bending stiffness to provide sufficient flexibility to track over a guidewire in the patient's distal tortuous vasculature.

The polymeric material of the biaxially oriented distal outer tubular member 23 is biaxially oriented by radially and longitudinally expanding an extruded tube used to form the distal outer tubular member 23, as discussed in more detail below.

The biaxially oriented distal outer tubular member 23 is formed of a relatively soft/low durometer polymeric material. The polymer preferably has a Shore durometer hardness of not greater than about 63 D to about 70 D. A variety of suitable nonporous polymeric materials can be used including polyether block amide (PEBAX) copolymers, polyurethanes, polyethylenes, and polyesters. The polymeric material can have various levels of crystallinity, and thus can be crystalline or noncrystalline. In a presently preferred embodiment, the polymer is a single polymer or copolymer (i.e., not a blend of two separate polymers). For example, a presently preferred polymer is PEBAX 63D, which has a Shore durometer hardness of about 63 D.

In a presently preferred embodiment, the distal outer tubular member 23 is a single-layered tubular member (i.e., not a multi-layered tube), formed of the biaxially oriented polymer tubing. The biaxially oriented distal outer tubular member 23 thus does not require multiple layers of different polymeric materials or reinforcements to provide the desired combination of characteristics. Additionally, unlike porous polymeric materials which are expanded during processing to produce a desired porosity, the biaxially oriented distal outer tubular member 23 is itself fluid tight (i.e., non-porous) and thus does not require a non-porous additional layer in order to hold the inflation fluid. Thus, due to the nature of the thermoplastic polymeric material, the tubular member formed therefrom is not porous, and the radial and longitudinal expansion does not render the tubular member porous. A single-layered tubular member provides ease of manufacture and avoids problems associated with multi-layered shafts such as layer delamination and thickness nonuniformities.

In the illustrated embodiment, the biaxially oriented distal outer tubular member 23 has a uniform outer diameter along the entire length of the tubular member 23. In one embodiment, the biaxially oriented distal outer tubular member 23 has an inner diameter of about 0.028 to about 0.029 inches, and an outer diameter of about 0.0325 to about 0.0335 inches along at least a section thereof. The length of the biaxially oriented distal outer tubular member 23 is typically about 15 to about 20 cm.

The rupture strength of the catheter shaft is important for insuring that the balloon 14 can be inflated to the desired high pressure during a medical procedure. If the relatively low durometer polymeric material was extruded to the final (expanded) dimensions of the biaxially oriented distal outer tubular member 23, the resulting tubular member would have a rupture strength which would be significantly lower than the desired value, and, for example, which would not be significantly greater than the balloon 14 rupture pressure. In the catheter 10 of the invention, the balloon rated burst pressure is significantly less than (e.g., about 4 atm less than, or about 20% less than) that of the biaxially oriented tubular outer member 23.

Figure 4:
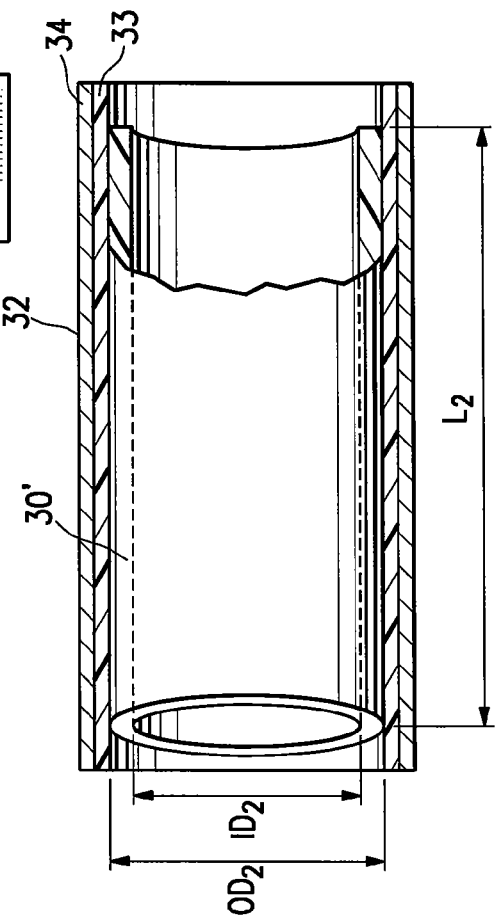
FIG. 4 illustrates the formation of the catheter shaft outer tubular member, in which an extruded tube is radially and longitudinally expanded in a capture member in a method embodying features of the invention, with the extruded tube shown prior to being radially and longitudinally expanded.
Figure 5:
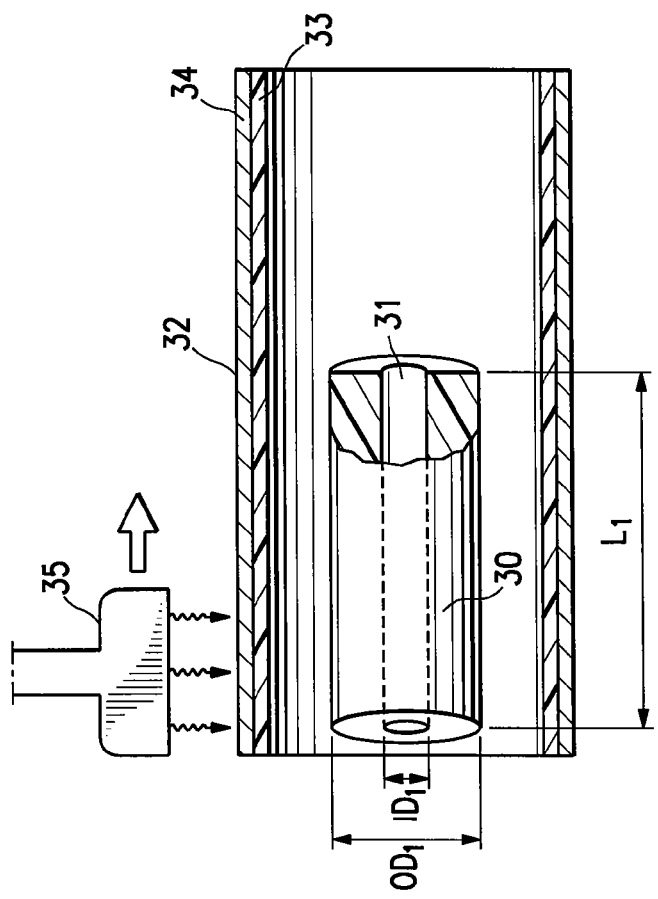
FIG. 5 illustrates the extruded tube of FIG. 4 after being radially and longitudinally expanded in the capture member.

FIGS. 4 and 5 illustrate a method of making a biaxially oriented tubular member such as the biaxially oriented distal outer tubular member 23 of the catheter 10 of FIG. 1. A method of the invention generally comprises melt-extruding a thermoplastic polymeric material having a relatively low Shore durometer hardness, to form a tube 30 having a lumen 31, a first inner and outer diameter ($ID_1$, $OD_1$) and a first length ($L_1$), and cooling the extruded tube 30 to a temperature (e.g., to room temperature) which is less than an elevated temperature of the melt-extrusion. The cooled extruded tube 30 is placed within a capture member 32, heated to an elevated temperature, and radially and axially expanded in the capture member 32 to a second inner and outer diameter ($ID_2$, $OD_2$) and length ($L_2$), to thereby biaxially orient the polymeric material of the extruded tube 30. FIG. 4 illustrates the extruded tube 30 disposed within the capture member 32 prior to being expanded therein, and FIG. 5 illustrates the expanded tube 30' within the capture member 32 (i.e., the extruded tube 30 of FIG. 4 after being radially and longitudinally expanded within the capture member 32). After being radially and longitudinally expanded, the resulting expanded tube 30' is cooled to room temperature and heat stabilized as discussed in more detail below. The catheter 10 is subsequently assembled, at least by sealingly securing a balloon to a distal end of the expanded tubular member such that the balloon has an interior in fluid communication with the expanded tubular member lumen.

The dimensions of the extruded tube 30 are set by the extrusion apparatus, and are typically not resized (e.g., hot die necked) prior to the radial and longitudinal expansion. For example, the tubular member is typically extruded by a screw extruder having a die and mandrel sized so that upon ordinary draw-down the tubular member exiting the extruder has the first outer diameter ($OD_1$), and the first inner diameter ($ID_1$).

In the embodiment of FIG. 4, the capture member 32 is tubular with an inner surface layer 33 of a lubricious polymeric material such as polytetrafluoroethylene (PTFE) for subsequent ease of part removal, reinforced with an outer high strength jacket layer 34 such as stainless steel tubing configured to prevent or inhibit diameter creep (growth) after repeated use. Thus, the capture member 32 is configured to radially restrain the growing tube 30, without the inner or outer diameter of the capture member 32 increasing at the elevated internal pressures used to radially expand the extruded tube 30.

The extruded tube 30 is heated to the elevated temperature within the capture member 32, which in the illustrated embodiment comprises directing heat from a heating nozzle 35 at the outer surface of the capture member 32. In a presently preferred embodiment, the heating nozzle 35 traverses along a length of the extruded tube 30, from a first end to the opposite end. Thus, the radial and longitudinal expansion is initiated with only the first end of the extruded tube 30 heated by the nozzle 35 in one embodiment. In a presently preferred embodiment, the extruded tube 30 is heated to an expansion elevated temperature which is less than the melt-extrusion elevated temperature (i.e., less than a melting temperature of the polymeric material).

The extruded tube 30 is axially expanded with a load applied on at least one end of the tube, e.g., using a vertical necking apparatus (not illustrated), and is radially expanded with pressurized media introduced into the extruded tube lumen from a pressurized media source (not illustrated) connected to one end of the extruded tube 30. Specifically, with the heating nozzle 35 heating the first end of the extruded tube 30, the heating nozzle 35 is moved toward the second end and the load is applied to the second end in the same direction as the heating nozzle movement to axially expand (i.e., stretch lengthwise) the extruded tube 30. The amount of the load required to provide the desired stretch percent depends on factors such as the tensile elongation, dimensions, material of the tubing 30, pressure of the pressurized media, and the expanded inner diameter. The pressurized media, e.g., compressed air, is at an elevated pressure sufficient to initiate the radial expansion, such that the wall hoop stress exceeds the material resistance (typically the yield stress) to stretching at the blowing temperature. The internal pressure used to radially expand the tubing 30 is typically about 400 to about 600 psi.

The extruded tube 30 is preferably simultaneously radially and axially expanded at the elevated temperature, for ease of manufacture. However, it can alternatively be sequentially expanded (i.e., first radially then longitudinally, or first longitudinally and then radially).

The tubing 30 is preferably radially expanded into contact with the inner surface of the capture member 31, to the second outer diameter which is about equal to the inner diameter of the capture member 31. The tubing 30 radially expands in all directions around the tubing circumference, resulting in circumferential orientation of the polymeric material. In a presently preferred embodiment, the second inner diameter ($ID_2$) is at least about 5 times larger than the first inner diameter ($ID_1$) of the extruded tube (i.e., the blow-up-ratio, BUR, of the expanded tubular member 30' is at least about 5, and is more specifically about 5.8 to about 6). The large BUR provides a high degree of circumferential orientation, for a large increase in the rupture pressure of the tubing. In one embodiment, the tubing is radially expanded to substantially the maximum amount possible (i.e., to a BUR which is at least about 80% of the maximum BUR possible). Specifically, as the tubing radially expands, the radius increases and the tubing wall thickness decreases, which results in a rapid increase in the wall hoop stress during constant pressure blowing. If the wall hoop stress of the growing tubing exceeds the ultimate hoop strength of the material, rupture will occur. As a result, there is a limit to the BUR (i.e., a maximum attainable BUR) of a polymeric material forming the tubing. The resulting expanded tubular member 30' exhibits little additional radial expansion at increasing internal pressures and preferably has a rupture mode consisting of a small longitudinally extending slit, for minimal vessel injury in the event of a shaft rupture. Within the working pressure range of the balloon 14, the biaxially oriented distal outer member 23 preferably has minimal radial growth, and as the pressure is increased above the rated burst pressure, the orientation preferably prevents the formation of a bulbous, highly expanded pocket along the biaxially oriented distal outer member 23 which can otherwise form as an outer member wall expands as the pressure therein approaches the rupture pressure.

Although the dimensions will vary depending upon the type of catheter and desired use of the biaxially oriented tubular member, the extruded first inner diameter ($ID_1$) is generally about 0.004 to about 0.006 inches and the extruded first outer diameter ($OD_1$) is generally about 0.021 to about 0.023 inches, whereas the expanded second inner diameter ($ID_2$) is generally about 0.028 to about 0.029 inches and the expanded second outer diameter ($OD_2$) is generally about 0.0325 to about 0.0335 inches.

The dimensions of the expanded tube 30' are typically stabilized after the radial and longitudinal expansion using a heat stabilization process in which the expanded tube 30' is heated for a duration at an elevated temperature sufficient to stabilize the polymeric material of the tube. In a presently preferred embodiment, the heat stabilization comprises heating the expanded tube 30' on a mandrel which controls the amount of radial shrinkage. Specifically, the expanded tube 30' is placed on a mandrel and reheated to a temperature above room temperature but typically below the expansion temperature to allow for radial recovery onto the mandrel and for the radial and axial dimensions to stabilize. The mandrel outer diameter is slightly smaller than the inner diameter of the expanded tubular member 30', to allow for slidably mounting the expanded tubular member 30' thereon. The amount of radial and axial shrinkage is relatively minimal, i.e., not greater than about 5%, and the heat stabilization preferably does not substantially decrease the rupture pressure of the tubular member. The heat stabilization temperature is typically significantly more than the polymeric glass transition temperature but less than the elevated temperature used during the radial and axial expansion. In a presently preferred embodiment, a PEBAX tubular member is heat stabilized at about 100 to about 140° C. for about 10 to about 15 minutes.

In one embodiment, the biaxial orientation of the polymer of the tubular member 30' is substantially uniform along the entire length thereof. Thus, the extruded tube 30 is radially expanded by a substantially uniform amount along the length thereof, and is longitudinally expanded by a substantially uniform amount, to produce an expanded tube 30' having a substantially uniform inner and outer diameter along the length thereof. For example, in the embodiment illustrated in FIGS. 4 and 5, the capture member 32 has a uniform inner diameter configured to radially restrain the expanding extruded tube 30 at the second outer diameter, such that the second outer diameter of the expanded tube 30' is uniform along the length of the expanded tube 30'. In an alternative embodiment, the inner diameter of the capture member varies along at least along a section of the capture member 32, to produce a tapered biaxially oriented tubular member, as discussed in more detail below. Ruler markings on the ends of the extruded tube 30 can be compared before and after the longitudinal expansion to confirm that the desired overall stretch percent is achieved. The amount of longitudinal expansion, expressed as a stretch percent, typically ranges from about 50 to about 200% of the initial length ($L_1$) of extruded tube 30. In the embodiment in which the expanded tube 30' has a substantially uniform inner and outer diameter along the entire length thereof, the axial stretch percentage is, more specifically, preferably about 75 to about 100% of the initial length ($L_1$).

The final expanded dimensions ($ID_2$, $OD_2$) are preferably predicted and controlled during formation of the expanded tubular member 30', to thereby provide a desired bending stiffness, rupture strength, tensile break load, and percent elongation to failure. During the radial and axial expansion, the inner diameter of the extruded tubing 30 increases due to both the internal pressure and the longitudinal stretching. Thus, extruded tubes having different wall thicknesses can be expanded to similar final expanded dimensions ($ID_2$, $OD_2$) using the same capture member 32 by using different stretch percentages. Moreover, significant characteristics of the resulting expanded tubular member can be tailored by selecting and controlling the nature of the extruded tube and amount of expansion. For example, the break load of the expanded tubular member can be increased by increasing the outer diameter of the starting extrusion ($OD_1$) and correspondingly increasing the stretch percent. The elongation to failure of the expanded tubular member can be increased by increasing the elongation of the starting extrusion.

In the embodiment of FIG. 1, the biaxially oriented distal outer tubular member 23 of catheter 10 has a uniform wall thickness and diameter (the biaxially oriented tubular member 23 preferably being the section of the shaft outer member which is located distal to the rapid exchange notch at guidewire proximal port 28). In alternative embodiments, the biaxially oriented tubular member is formed with at least a section having a tapering wall thickness and/or diameter.

FIG. 6 illustrates a balloon catheter 110 which has a tapered biaxially oriented distal outer tubular member 123 with a diameter and wall thickness that are distally tapering (i.e., decreasing in a distally extending direction). The balloon catheter 110 generally comprises an elongated shaft 111 having a proximal end, a distal end, a guidewire lumen 21 and an inflation lumen 20 extending therein, an inner tubular member 124 with the guidewire lumen 21 therein, and a proximal outer tubular member 122 with a proximal portion of the inflation lumen 20 therein, and a distal outer tubular member 123 which has a distal portion of the inflation lumen 20 therein and which is formed of a tapered biaxially oriented nonporous thermoplastic polymer. A balloon 14 sealingly secured to a distal shaft section has a proximal skirt secured to the distal outer tubular member 123 and a distal skirt secured to the inner tubular member 124 such that an interior of the balloon is in fluid communication with the inflation lumen 20. An adapter 118 on the proximal end of the shaft 111 is configured to provide access to the guidewire lumen 21 and has an arm 119 configured for connecting to a source of inflation fluid (not shown) for inflating the balloon 14. In the illustrated embodiment, the balloon catheter 110 has a stent 115 releasably mounted on the balloon 14 for delivery and deployment within a patient's body lumen, although the catheter 110 can be configured for a variety of uses including angioplasty, drug delivery and the like. The stent delivery balloon catheter 110 is an over-the-wire type catheter, and thus has the guidewire lumen 21 extending the entire length of the catheter shaft 111 to a proximal port at the proximal end of the catheter, unlike the rapid exchange type catheter 10 of the embodiment of FIG. 1 having a guidewire proximal port 28 distal to the proximal end of the catheter 10. The catheter 110 is otherwise similar to the catheter 10 of the embodiment of FIG. 1, such that the discussion above relating to the biaxially oriented tubular member formed of a relatively low durometer material yet having a relatively high rupture pressure applies as well to the embodiment of FIG. 6.

The tapered biaxially oriented distal outer tubular member 123 has a first (distal) section 130 with a uniform wall thickness and diameter, and a second (proximal) section 131 with a wall thickness and outer diameter tapering distally from the proximal end of the distal outer tubular member 123, as best illustrated in FIG. 7 showing an enlarged longitudinal cross section taken within line 7-7 of FIG. 6.

The distal section 130 of the biaxially oriented distal outer tubular member 123 extends from the tapering proximal section 131 to the distal end of the biaxially oriented distal outer tubular member, and has a constant inner and outer diameter and a constant wall thickness along substantially its entire length (i.e., constant within normal manufacturing tolerances). The tapering proximal section 131 similarly has a constant inner diameter, such that the inner diameter is constant along the entire length of the biaxially oriented distal outer tubular member 123 in the embodiment of FIG. 6.

The proximal end of the tapering proximal section 131 is bonded, typically by fusion and/or adhesive bonding, to the distal end of a proximally adjacent section of the shaft (e.g., to the proximal outer tubular member 122), and the tapered proximal section 131 extends distally of the bond. The tapered proximal section is generally about 2% to about 80% of the length of the tapered biaxially oriented tubular member 123 of over-the-wire catheter 110, and specifically, in the embodiment illustrated in FIG. 7, the tapered proximal section 131 is about 40% of the length of the tapered biaxially oriented tubular member 123. However, the taper can be a more abrupt shorter taper, or a more gradual taper extending along a longer length or along essentially the entire length of the biaxially oriented tubular member 123.

The taper length of a tapered biaxially oriented tubular member would typically be longer in an over-the-wire balloon catheter compared to a rapid exchange balloon catheter due at least in part to the affect of the formation of the rapid exchange notch (i.e., at proximal guidewire port 28 in the embodiment of FIG. 1) of a rapid exchange catheter. Specifically, forming the rapid exchange notch typically requires heat and radially inward force to bond the tubular members together at the proximal guidewire port 28, which would change the biaxial orientation and tapering of the tubular member. As a result, in a rapid exchange catheter, the biaxially oriented tubular member, and more specifically the tapered section of the biaxially oriented tubular member, is preferably located distal to the proximal guidewire port 28. Expressed as a percentage of the total length of the shaft 111, the length of the tapered section 131 is generally about 1% to about 20% of the total length of the shaft 111 of the over-the-wire type catheter 110 of FIG. 6 (from the proximal to the distal end of the catheter). In contrast, in a rapid exchange type catheter such as catheter 10 of FIG. 1, a tapered section of the biaxially oriented distal outer tubular member is generally about 1% to about 15% of the length of the shaft (or generally about 5% to about 90% of the length of the biaxially oriented distal outer tubular member 23 of rapid exchange catheter 10).

In a presently preferred embodiment, the catheter 110 does not have a separate midshaft outer tubular member of intermediate stiffness to transition from the relatively stiff proximal shaft section to the relatively flexible distal shaft section. Rather, the tapered section 131 of biaxially oriented outer tubular member 123 provides a sufficiently large change in bending stiffness therealong that the proximal end of the biaxially oriented distal outer member 123 is secured directly to the distal end of the relatively stiff proximal outer member 122. The bending stiffness of the tapered biaxially oriented tubular member typically decreases distally along the length of the taper by about 20% to about 80%, more preferably by about 40% to about 80% (the 80% decrease corresponding to a percent increase (proximally) of about 350%). Thus, the bending stiffness changes along an integral, one-piece tubular member (tapered biaxially oriented tubular member 123), without requiring variable reinforcements such as braids, coils, sleeves, or multiple layers along the tubular member 123 to vary the bending stiffness therealong.

In a presently preferred embodiment, in order to provide a relatively large bending stiffness change along the length of the taper, the wall thickness in addition to the diameter of the biaxially oriented tubular member varies along the length of the taper. Preferably, the wall thickness of the tapered biaxially oriented tubular member 123 increases by about 50% to about 250% proximally along the tapered section 131, and as a result the bending stiffness of tapered tubular member 123 increases proximally by at least about 65%, and more preferably about 100% to about 350%, and more specifically by about 200% to about 350% therealong. For example, in one embodiment of tapered tubular member 123 having an inner diameter of about 0.7 mm, the wall thickness along constant wall thickness section 130 is about 0.05 mm to about 0.06 mm, and the wall thickness increases to a maximum of about 0.14 mm to about 0.16 mm at the proximal end section of the tapered section 131, such that the bending stiffness increases proximally by as much as about 340% (corresponding to a decreases distally of as much as about 78%). The inner diameter of tubular member 123 is typically about 0.65 mm to about 0.75 mm.

In a method of making a tapered biaxially oriented tubular member, the extruded tube is biaxially oriented as discussed above in relation to the embodiment of FIGS. 4 and 5. However, in a presently preferred embodiment, at least a section of the extruded tube is tapered during the biaxial orientation, preferably by varying the overall axial load that produces the axial orientation of the polymeric material of the tube. Specifically, the extruded tube is placed in a capture member similar to the capture member 32 of FIG. 4, and biaxially oriented by being heated with an external heat supply traversing longitudinally from a first to a second section of the tube and radially expanded with pressurized media in the tube lumen, and simultaneously axially expanded with an overall axial load that is controllably varied as at least a section of the tube is heated. As a result, different longitudinal portions along the length of a given biaxially oriented tubular member are thereby axially stretched by different amounts. Generally, the axial stretch percentage of the different longitudinal portions of the resulting tapered biaxially oriented tubular member varies from about 50% to about 300% of the initial length of the tube portion. Preferably, varying the overall axial load comprises varying an external load (e.g., weight) applied on one end of the tube. However, in one embodiment, the overall axial load is varied by additionally or alternatively varying the pressure of the pressurized media in the tube lumen.

In one presently preferred embodiment, the tapered biaxially oriented tubular member is biaxially oriented in a capture member which tapers from a larger to a smaller inner diameter along at least a section of the capture member. FIG. 9a illustrates extruded tube 30, prior to being biaxially expanded, in a tapered capture tube 132 having a uniform inner diameter along a first section 133 extending from a first end of the capture member, and having a tapered inner diameter along a second section 134 extending from a second end of the capture member to the uniform diameter first section 133. The overall axial load is decreased as the heat supply (typically a heating nozzle 35) traverses along the tapered section 134 of the capture member 132 from the smaller to the larger inner diameter ends of tapered section 134.

Preferably, the inner diameter contour of the tapered capture member corresponds to the desired expanded outer diameter profile of the tapered biaxially oriented tubular member. Thus, by increasing the inner diameter of the capture tube 132 along section 134, a biaxially oriented tubular member can be formed which has a tapered outer diameter, such as tubular member 123 of the embodiment of FIG. 6. In order to provide the constant inner diameter of tapered biaxially oriented tubular member 123, the external weight (or overall axial load) is constant as the heating nozzle 35 traverses along section 133, and is controllably varied by a particularly specified amount as the heating nozzle 35 traverses along tapered section 134 of the tapered capture tube 132, and FIG. 9b illustrates the resulting tapered biaxially expanded tube 30' within the capture member 132. As a result, although the extruded tube 30 will radially expand to a larger diameter along tapered section 134 of the tapered capture member 132, the corresponding thinning of its wall thickness which would otherwise occur is prevented by reducing the axial stretch percentage. The resulting tapered biaxially oriented distal outer member 123 has an axial orientation that increases distally along the tapered proximal section and has a circumferential orientation that is substantially uniform along the entire length of the biaxially oriented tubular member 123 at least within a radial inner surface portion thereof. To produce the tapered biaxially oriented tubular member 123 of the embodiment of FIG. 7, after expansion of the tube 30 in the tapered capture member 132, the as-expanded tubular member is typically heat stabilized, preferably on a constant outer diameter mandrel (see e.g., the mandrel 146 of FIG. 12) as discussed in more detail below.

The axial external weight values which are required to prepare a desired tapered biaxially oriented tubular member are predicted based on calculated axial stretch percentages and calculated total axial stress values for an extruded tube 30 of a given as-extruded inner and outer diameter. By selecting the varying external weight values applied to the tube 30, the resulting biaxially expanded tubular member can be caused to have a variety of different tapering configurations. For example, as tube 30 is expanded in the tapered capture member 132, the external weight decreases by a relatively large amount (see below Example 2) in order to provide the tapered biaxially oriented tubular member 123 of FIG. 7 having a tapering outer diameter and wall thickness but a constant inner diameter. In contrast, if the external weight was instead decreased by a lesser amount in the tapered capture member 132, a tapered biaxially oriented tubular member 135 could be prepared which has a tapering inner and outer diameter, as illustrated in FIG. 10. In the embodiment of FIG. 10, the tapered biaxially oriented tubular member 135 has a proximal end 136, a distal end 137, a nontapering distal section 138, and a tapering proximal section 139 with a distally tapering inner and outer diameter and a constant wall thickness. Tapered biaxially oriented tubular member 135 of the embodiment of FIG. 10 is typically less preferred than the embodiment of FIG. 7 due to the relatively small change in bending stiffness readily produced without varying the wall thickness of the tubular member 135. However, the increased inner diameter along the tapered proximal section 139, relative to tapered proximal section 131 of the embodiment of FIG. 7, is preferred in a catheter in which a large lumen size is more important to catheter performance than a large change in bending stiffness provided by the tapered wall thickness of the biaxially oriented tubular member.

Thus, the biaxially oriented tubular member can be provided with a variety of different tapering configurations. For example, FIG. 11 illustrates a tapered biaxially oriented tubular member 140 having a first end 141, a second end 142, a nontapering first section 143, and a tapering second section 144 with a constant outer diameter and an inner diameter which tapers toward the second end 142 of the tubular member 140. As a result, the wall thickness (and bending stiffness) increases along the length of section 144 from the nontapering first section 143 to a larger wall thickness at the second end 142 of the tubular member 140 (i.e., the wall thickness increases inversely to the decreasing inner diameter of the tapered biaxially oriented tubular member 140). The tapered tubular member 140 can be prepared in a uniform diameter capture member 32 during biaxial orientation of the extruded tube 30, by applying a constant axial weight as the heating nozzle 35 traverses along the first section of the extruded tube 30, and then gradually decreasing the axial weight as the heating nozzle 35 traverses along the second section of the extruded tube 30.

By varying the tension along the length to form the taper during biaxial orientation, the method of the invention facilitates localized compensation for dimensional and property variability within the original as-extruded tube 30 (i.e., adjusting for lot-to-lot material property variation).

A tapered biaxially oriented tubular member of the invention generally has a bending stiffness that decreases by the relatively large amount of a factor of about 2 to about 4 along the length of the tapering section, which is provided by varying the wall thickness and the diameter of the biaxially oriented tubular member along the length of the tapering section. The change in bending stiffness (moment of inertia) is preferably linear, or substantially linear (i.e., within normal manufacturing tolerance), and the uniform taper is specifically provided with desired dimensions at a desired location along the biaxially oriented tubular member using a method of the invention.

As discussed above in relation to the embodiment of FIG. 1, a biaxially oriented tubular member of the invention is typically heat stabilized after the biaxial expansion by being heated on a mandrel. In one embodiment, the method of producing the tapered biaxially oriented tubular member takes advantage of the diameter shrinkage that occurs during the heat stabilization. For example, provided the heat stabilization time and temperature are sufficient to radially shrink the expanded tubular member by a desired amount, heat stabilizing the tapered biaxially oriented tubular member 140 of FIG. 11 on a constant diameter mandrel 146 provides a resized tapered biaxially oriented tubular member 145 having a constant inner diameter and a variable outer diameter and wall thickness, as illustrated in FIG. 12. However, the heat stabilization process induces both radial and axial shrinkage which leads to greater wall thickening in sections having greater initial clearance between the as-expanded inner diameter and the mandrel outer diameter. As a result, a tubular member that is biaxially expanded to an inner diameter profile substantially equal to the final target and heat stabilized on a mandrel having a corresponding outer diameter closely matched thereto is preferred in order to minimize the amount of shrinkage, to thereby provide for improved dimensional control. Therefore, although a uniform diameter (nontapered) biaxially oriented tubular member can be provided with a taper after the biaxial expansion merely by shrinking onto a tapered mandrel during heat stabilization, such a method is much less preferred than a method in which the tubular member is tapered during the biaxial expansion (e.g., by varying the axial weight applied during the biaxial expansion within a tapered capture member). Moreover, without a tapered capture member (e.g., member 132), the range of possible dimensional combinations in the finished tapered biaxially oriented tubular member is relatively limited.

Thus, heat stabilization on a mandrel with a profile which closely matches the as-expanded tapered biaxially oriented tubular member's inner diameter not only provides the expected dimensional stability which comes from radial recovery of the expanded tube onto the mandrel, but also improved dimension control by avoiding inconsistencies in the as-expanded inner diameter. Specifically, the finished heat stabilized tube has tight inner diameter tolerances that match those of the heat stabilization mandrel, and outer diameters that are less variable than before the heat stabilization. For example, in one embodiment, tapered biaxially oriented tubular member 123 has an inner diameter of about 0.77+/−0.04 mm before heat stabilization, and of about 0.725+/−0.005 mm after heat stabilization on a mandrel.

The heat stabilization mandrel has an outer diameter that is less than the inner diameter of the tapered biaxially oriented tubular member to allow the mandrel to be slid therein, but is preferably not more than about 10% less than the inner diameter of the as-expanded (before heat stabilization) tapered biaxially oriented tubular member.

To prepare a tapered biaxially oriented tubular member according to a method of the invention, a combination of experimental and analytical methods can be used in order to predict the varying diameter/wall thickness of the resulting tapered biaxially oriented tubular member. The experimental and analytical methods take into account a number of factors such as the external axial load, capture member inner diameter, and the actual deformation behavior of the extruded tube 30 during its brief exposure to the moving heat source (nozzle 35). For example, a number of samples of extruded tubes 30 were biaxially oriented with radially expansive gas pressure and a varying external weight, and the total axial stress was calculated and the actual axial expansion was experimentally observed. The total axial stress was calculated by first calculating the total axial load, which is the sum of the external weight and the axial load due to the gas pressure within the tube 30. The axial load due to the gas pressure within the tube is based on the as-expanded inner diameter, which is calculated using the as-extruded dimensions, the as-expanded outer diameter, and the axial expansion percentage for a constant gas pressure of, e.g., 475 psig.

Figure 13:
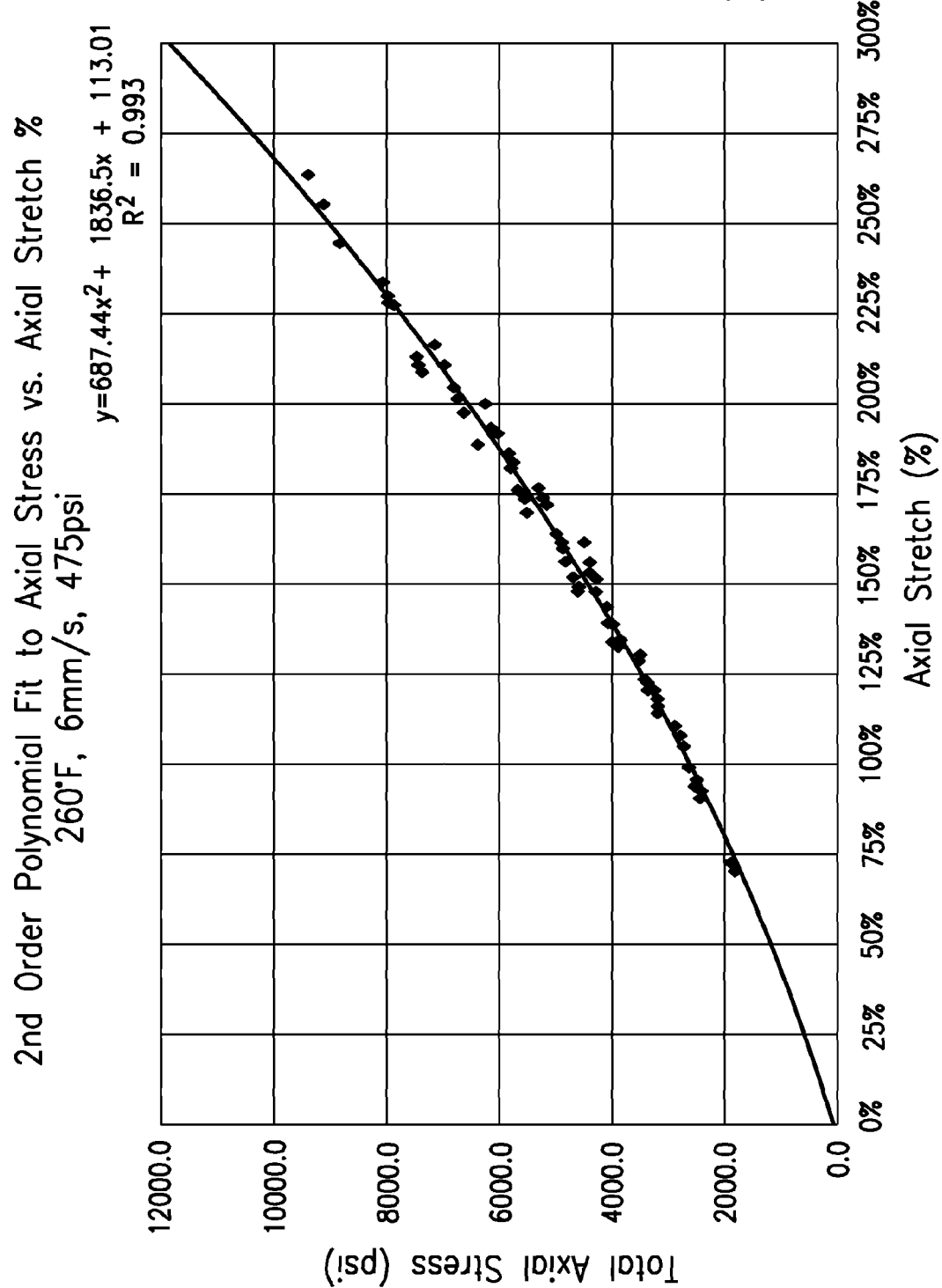
FIG. 13 illustrates the second order polynomial fit to total axial stress as a function of axial stretch percentage, for experimentally and analytically derived data for biaxially oriented tubing according to a method embodying features of the invention.

A second order polynomial was fit to a plot of the calculated total axial stress vs. observed axial expansion percentage, as illustrated in FIG. 13. The second order polynomial had an R-squared value of 0.993, and therefore may be used as an effective method for predicting axial expansion percentage (and thus wall thickness) after biaxial expansion. The second order polynomial mathematically defines the relationship between the stress and strain in the axial direction for a particular polymer tube under a specific set of experimental conditions, and can be used to predict the external axial load necessary to produce a given wall thickness during biaxial expansion into a known capture member size.

To make the external axial load predictions, typically the as-extruded outer and inner diameters are selected and the target final outer and inner diameter values are identified at various locations along the length of the tubular member. The first step is then to determine the required stretch percentages at locations of interest per the following formula where $OD_1$ and $ID_1$ are as-extruded tube dimensions, and $OD_2$ and $ID_2$ are the expanded dimensions at a given location:

$$\text{Stretch Percentage} = 100 \times [(OD_1^2 - ID_1^2)/(OD_2^2 - ID_2^2) - 1] \quad \text{Eq. 1}$$

Using the calculated stretch percentage values, the associated total axial stress values (S) are then determined using the experimentally derived polynomial, where a, b, and c are the coefficients obtained from fitting a second order polynomial to experimental data (in FIG. 13 they are 687.44, 1836.5, and 113.01, respectively):

$$S(\text{total}) = a \times (\text{Stretch \%})^2 + b \times (\text{Stretch \%}) + c \quad \text{Eq. 2}$$

Using the total axial stress determined via equations 1 and 2, the necessary external weight (W) at each location can be predicted using the following equation:

$$W = [S(\text{total}) - (P \times ID_2^2)/(OD_2^2 - ID_2^2)] \times [(3.14159/4) \times (OD_2^2 - ID_2^2)] \quad \text{Eq. 3}$$

The resulting prediction of external weight for each location of interest is then used to prepare a tapered biaxially oriented tubular member having specific, desired dimensions. In one embodiment, the production is automated by programming the predicted external weight values into a closed loop feedback-controlled tension system so that the applied external weight is controllably varied as a function of axial location (i.e., the position of the traveling heat source). Alternatively, an operator can manually adjust the applied external axial weight during the biaxial expansion process.

The following examples illustrate the formation of biaxially oriented tubular members in accordance with embodiments of the invention.

Example 1

PEBAX 63D was used to extrude four sets of multiple tubing samples (N=5) having an extruded inner diameter (ID) of about 0.005 inches, and an extruded outer diameter (OD) ranging from about 0.0217 inches to about 0.0264 inches. The extruded tubing was placed inside a stainless steel capture tube having a Teflon liner with an ID of about 0.034 inches, and radially and axially expanded therein at an elevated temperature. Specifically, a vertical hot air necking apparatus was used to pressurize the tubing with pressurized air at about 500 psi and to simultaneously lengthen the tubing with an axial load pulling on one end of the tubing, while the tubing was heated within the capture tube using a heating nozzle traversing along the outside of the capture tube at a set point of about 385° F. (196° C.) (the temperature within the inner chamber of the capture tube is typically less than the set point, and depends upon factors such as the nozzle temperature set point, the nozzle speed, the nozzle air flow rate, and the capture tube materials and dimensions). The resulting biaxially oriented expanded tubular member samples had similar final dimensions of about 0.0285 inch ID and 0.033 inch OD, and a relatively high rupture pressure of not less than about 600 psi, and relatively low Gurley bending stiffness of about 102 mg or less. The average longitudinal stretch percentage, and the mean rupture pressure, Gurley bending stiffness, and tensile load of the resulting tubular member samples, following stabilization at 100° C./15 minutes on a 0.028-0.0285 inch mandrel, are given below in Table 1.

TABLE 1

| | Extruded ID (in) | Extruded OD (in) | Avg. Stretch (%) | Bending Stiffness Gurley Units (mg) | Mean Rupture Pressure (psi) | Tensile Break Load (lbf) |
|---|---|---|---|---|---|---|
| Extrusion Lot No. 1 (N = 5) | 0.0057 | 0.0217 | 85 | 97.2 | 665 | 2.28 |
| Extrusion Lot No. 2 (N = 5) | 0.0054 | 0.0235 | 113 | 102.2 | 697 | 2.56 |
| Extrusion Lot No. 3 (N = 5) | 0.0053 | 0.0249 | 140 | 92.9 | 664 | 3.49 |
| Extrusion Lot No. 4 (N = 5) | 0.0057 | 0.0264 | 166 | 88.8 | 606 | 3.91 |

Extruding a soft material such as PEBAX 63D directly to the final dimensions (0.0285 inch ID, 0.033 inch OD) would be expected to produce a tubular member having an unacceptably low rupture and tensile strength for use as the shaft tubular member. By way of comparison, tubular members of PEBAX 72D extruded directly to the final dimensions of about 0.028 inch ID and 0.032 inch OD, and similarly stabilized at 100° C./15 min., had a Gurley Bending Stiffness of about 223.1 mg, and a mean rupture pressure of about 436 psi. It should be noted that PEBAX 72D has a higher durometer than the PEBAX 63D, so that the higher bending stiffness is to be expected. Increasing the wall thickness in a second set of PEBAX 72D comparison tubular members, which is expected to increase the rupture pressure and bending stiffness of the tubing (specifically, the tubing had extruded dimensions of about 0.031 ID and 0.037 inch OD, and was similarly stabilized at 100° C./15 min.), increased the mean rupture pressure of the comparison tubular members to about 499 psi, but also (disadvantageously) increased the Gurley Bending Stiffness to 258.6 mg. Although this bending stiffness would be expected to decrease with a lower durometer material (e.g., PEBAX 63D), a corresponding decrease in the rupture pressure, with large radial growth prior to rupture, would also be expected.

Example 2

Equation 3 was used to predict the external weight values required to make a variable outer diameter, constant inner diameter tubular member such as the tapered biaxially oriented tubular member 123 of FIG. 7. The predicted external weight values (using Eq. 3) are tabulated in Table 2 along with the desired as-extruded and final expanded dimensions, the calculated stretch percentages (using Eq. 1), and the calculated total axial stress values (using Eq. 2). In the example set forth in Table 2, the as-expanded outer diameter and wall thickness is to be held constant over the first 20 cm, and then increased linearly over the remaining length. The internal pressure during the biaxial expansion tapering procedure was constant at 475 psi.

TABLE 2

| Axial Location (cm) | ID1 (cm) | OD1 (cm) | ID2 (cm) | OD2 (cm) | Axial Stretch (%) | Stress S(total) (psi) | External Weight (grams) |
|---|---|---|---|---|---|---|---|
| 0 to 20 | 0.016 | 0.074 | 0.073 | 0.0838 | 229.6 | 7956 | 560.6 |
| 22 | 0.016 | 0.074 | 0.073 | 0.0848 | 197.8 | 6433 | 487.0 |
| 24 | 0.016 | 0.074 | 0.073 | 0.0858 | 171.2 | 5272 | 423.9 |
| 26 | 0.016 | 0.074 | 0.073 | 0.0868 | 148.8 | 4366 | 368.9 |
| 28 | 0.016 | 0.074 | 0.073 | 0.0878 | 129.5 | 3646 | 320.3 |
| 30 | 0.016 | 0.074 | 0.073 | 0.0889 | 112.9 | 3063 | 276.7 |
| 32 | 0.016 | 0.074 | 0.073 | 0.0899 | 98.4 | 2584 | 237.1 |
| 34 | 0.016 | 0.074 | 0.073 | 0.0909 | 85.5 | 2187 | 201.0 |
| 36 | 0.016 | 0.074 | 0.073 | 0.0919 | 74.2 | 1853 | 167.5 |
| 38 | 0.016 | 0.074 | 0.073 | 0.0929 | 64.0 | 1569 | 136.4 |
| 40 | 0.016 | 0.074 | 0.073 | 0.0939 | 54.8 | 1327 | 107.3 |

The as-expanded outer diameter set forth in Table 2 is the result of a capture member, such as tapered capture member 132, having an inner diameter contoured to correspond to the desired expanded outer diameter of the biaxially oriented tubular member. The as-expanded inner diameter is to be held constant over the entire length by controllably varying the external weight. The predicted external weight is diminished from approximately 560 grams to approximately 107 grams, and the predicted diminishment of weight is nearly linear. As a result, the actual weight decline could be made linear with minimal impact on the resulting dimensions of the tapered section of the tubular member.

Example 3

To make a variable outer diameter, variable inner diameter, constant wall thickness tubular member such as the tapered biaxially oriented tubular member 135 of FIG. 10, the same conditions as in Example 2 are used, but the external weight decreases by a smaller amount from the 20 cm to the 40 cm axial location. Specifically, to maintain a constant wall thickness of 0.004 inches (0.01 cm) as the outer diameter of the tube increases as in Example 2 from 0.0838 to 0.0939 cm, the axial stretch percentage, total stress, and external weight decrease as set forth in Table 3.

TABLE 3

| Axial Location (cm) | Axial Stretch (%) | Stress (S) (total) (psi) | External Weight (grams) |
|---|---|---|---|
| 0-20 | 229.6 | 7956 | 560.6 |
| 22 | 225.4 | 7747 | 547.1 |
| 24 | 221.4 | 7547 | 533.7 |
| 26 | 217.4 | 7353 | 520.4 |
| 28 | 213.5 | 7166 | 507.4 |
| 30 | 209.7 | 6986 | 494.4 |
| 32 | 206.0 | 6812 | 481.06 |
| 34 | 202.3 | 6644 | 468.9 |
| 36 | 198.8 | 6481 | 456.3 |
| 38 | 195.4 | 6324 | 443.8 |
| 40 | 192.0 | 6172 | 431.4 |

Figure 14:
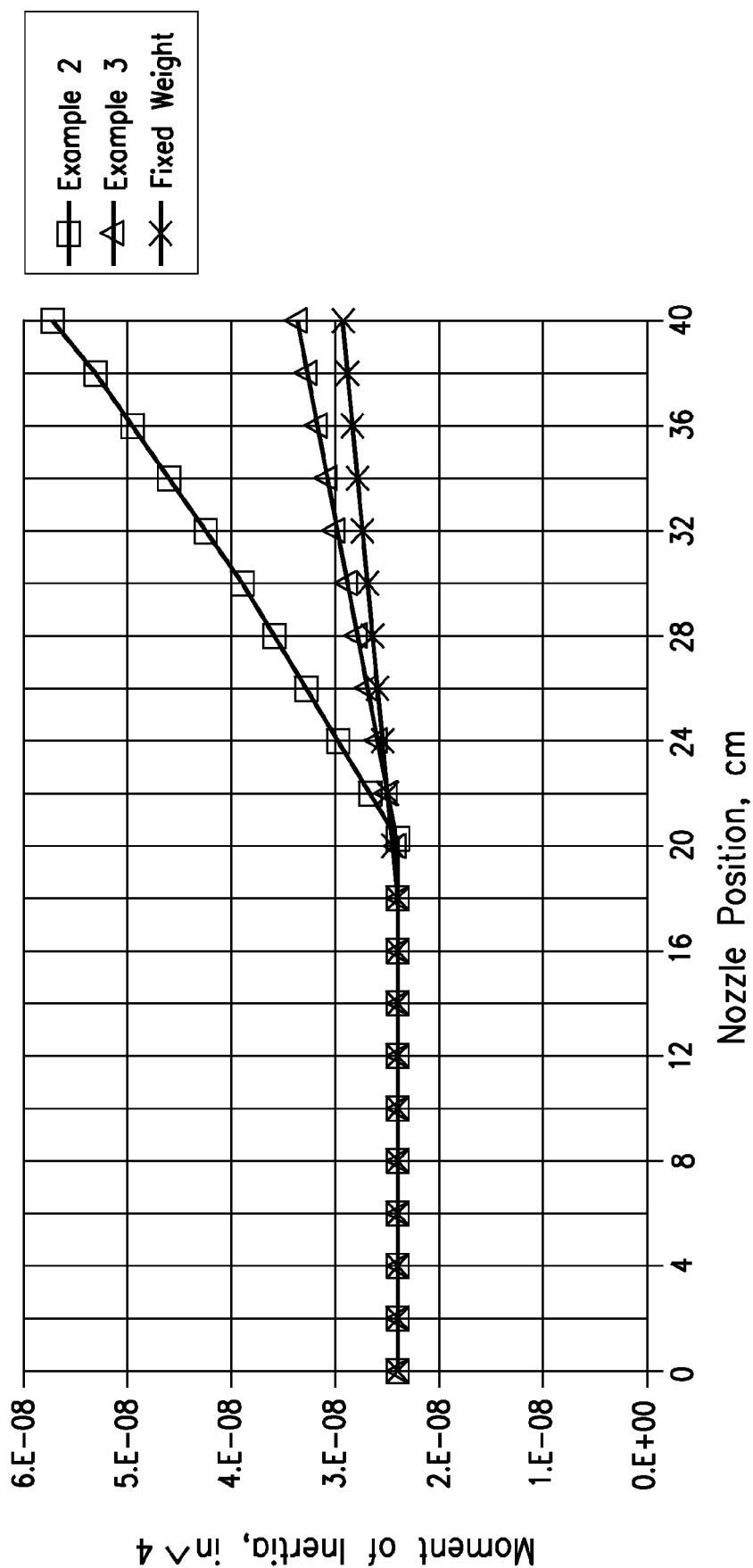
FIG. 14 is a graph of the predicted moment of inertia as a function of nozzle position for various tapered biaxially expanded tubular members.

The bending moment of inertia (I) can be calculated using the engineering formula for a hollow cylindrical beam, $I=(3.14159/64) \times (OD_2^4 - ID_2^4)$. FIG. 14 is a graph of the resulting calculated moment of inertia values plotted as a function of nozzle position for Examples 2 and 3. The graph includes also a comparison example in which the same initial external weight and tapered capture member profile as in Examples 2 and 3 would be used, but the external weight would be held constant throughout the biaxial expansion. The initial value of I is about $2.35 \times 10^{-8}$ for all three samples, and for Example 2 it increases to about $5.728 \times 10^{-8}$ whereas it increases a smaller amount to about $3.378 \times 10^{-8}$ for Example 3, and to about $2.951 \times 10^{-8}$ for the fixed weight comparison example.

Thus, as illustrated in FIG. 14, the greatest overall increase in bending stiffness occurs with the tapered biaxially expanded tubular member of Example 2, in which the wall thickness increases along with the increase in outer diameter of the expanded tubular member. Example 3 has substantially less gain in stiffness along the tapered region of the expanded tubular member, because its wall thickness is constant as the outer diameter increases. The stiffness profile for the fixed weight comparison example has even less gain because, without decreasing the external weight to account for the rising outer diameter, the wall thickness of the expanded tubular member must become thinner as its outer diameter increases. Specifically, the moment of inertia increases by about 144% for Example 2, and about 44% for Example 3, and about 25.5% for the fixed weight comparison example. Thus, the tapered biaxially oriented tubular member of Example 2 can provide the greatest change in stiffness for a fixed material durometer hardness and given tapering transition length, resulting in an improved transition from a highly flexible distal shaft section to a substantially more rigid proximal shaft section of a catheter of the invention.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

We claim:

1. A balloon catheter, comprising
   a) an elongated shaft having a proximal section and a tubular member attached thereto with an inflation lumen extending there through, wherein said tubular member is formed of a biaxially oriented nonporous thermoplastic polymer having a Shore durometer hardness of less than about 75D and has at least a section with a diameter tapering distally over a length of at least about 30% of the length of the tubular member such that the tapering section has a bending stiffness that decreases distally by about 20% to about 80% therealong; and
   b) a balloon sealingly secured to said tubular member, which has an interior in fluid communication with the inflation lumen, and a rupture pressure which is less than the rupture pressure of the shaft tubular member.

2. The catheter of claim 1 wherein the taper length is greater than about 10 cm.

3. The catheter of claim 1 wherein the taper length is about 30 to about 65% of the length of the tubular member.

4. The catheter of claim 1 wherein the tapered section of the biaxially oriented tubular member has a distally tapering wall thickness and outer diameter, and the bending stiffness increases proximally by at least about 65% therealong.

5. The catheter of claim 1 wherein the tapered section of the biaxially oriented tubular member has a distally tapering inner diameter and a distally tapering outer diameter, and a substantially constant wall thickness.

6. The catheter of claim 1 wherein the biaxially oriented tubular member bending stiffness decreases substantially linearly along the tapering section.

7. The catheter of claim 1 wherein the biaxially oriented tubular member of the shaft is a distal outer member which has a distal end sealingly secured to the balloon and a proximal end sealingly secured to a proximal tubular member, and the bending stiffness decreases by a factor of about 2 to 4.5 along the length of the tapering section.

8. The catheter of claim 7 wherein the catheter is an over-the-wire catheter with a guidewire lumen proximal port at a proximal end of the catheter, and the tapered section has a proximal end at the proximal end of the biaxially oriented tubular member of the shaft.

9. A balloon catheter, comprising
a) an elongated shaft having a proximal outer tubular member that is attached to a distal outer tubular member having an inflation lumen extending therein, an inner tubular member with a guidewire lumen extending therein, wherein said inner tubular member is disposed within at least a portion of said inflation lumen, wherein said proximal outer tubular member has a constant bending stiffness and said distal outer tubular member is formed of a biaxially oriented nonporous thermoplastic polymer having a Shore durometer hardness of less than about 75D, and which has a distal section, and a tapering proximal section with a length of at least about 30% of the length of the distal outer tubular member and with a wall thickness tapering distally such that a bending stiffness of the distal outer tubular member increases proximally by at least about 65% along the tapering proximal section; and
b) a balloon which has a proximal skirt sealingly secured to the distal outer tubular member and a distal skirt secured to the inner tubular member such that an interior of the balloon is in fluid communication with the inflation lumen, and a rupture pressure which is less than the rupture pressure of the distal outer tubular member.

10. The balloon catheter of claim 9 wherein the distal section of the biaxially oriented distal outer tubular member extends from the tapering proximal section to the distal end of the biaxially oriented distal outer tubular member, and the distal section of the biaxially oriented distal outer tubular member has a constant inner and outer diameter and a constant wall thickness along substantially its entire length.

11. The balloon catheter of claim 9 wherein the bending stiffness of the distal outer tubular member decreases by a factor of about 2 to 4.5 along the length of the tapering proximal section.

12. The balloon catheter of claim 9 wherein the tapering proximal section of the biaxially oriented distal outer tubular member has a constant inner diameter, and a distally tapering outer diameter.

13. The balloon catheter of claim 12 wherein the bending stiffness of the distal outer tubular member increases proximally by about 200 to about 350% along the tapering proximal section.

14. The balloon catheter of claim 9 wherein the length of the tapering proximal section of the distal outer tubular member is at least about 10 cm.

15. The balloon catheter of claim 9 wherein the tapering proximal section of the biaxially oriented distal outer tubular member has a constant outer diameter, and a distally increasing inner diameter.

16. The balloon catheter of claim 9 wherein the biaxially oriented tubular member bending stiffness decreases substantially linearly along the tapering proximal section.

17. The catheter of claim 9 wherein the biaxially oriented distal outer member has an axial orientation that increases distally along the tapering proximal section, and has a circumferential orientation that is substantially uniform along the entire length of the biaxially oriented distal outer member at least within a radial inner surface portion thereof.

18. The catheter of claim 9 wherein the tubular member has a Gurley bending stiffness of not greater than about 50 to about 150 mg, a rupture pressure of at least about 20 to about 50 atm, and a tensile break load of at least about 1 to about 5 lbf.

19. The catheter of claim 9 wherein the balloon is a relatively high pressure balloon having a rated burst pressure of about 14 to about 25 atm, and the rupture pressure of the biaxially oriented tubular member is about 20 to about 50 atm.

* * * * *